US007276599B2

(12) United States Patent
Moore et al.

(10) Patent No.: US 7,276,599 B2
(45) Date of Patent: Oct. 2, 2007

(54) OLIGONUCLEOTIDE SYNTHESIS WITH ALTERNATIVE SOLVENTS

(75) Inventors: Max N. Moore, Encinitas, CA (US); Mark Andrade, Vista, CA (US); Recaldo Carty, Carlsbad, CA (US); Anthony Scozzari, Vista, CA (US); Achim Krotz, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 494 days.

(21) Appl. No.: 10/858,917

(22) Filed: Jun. 2, 2004

(65) Prior Publication Data

US 2005/0026192 A1     Feb. 3, 2005

Related U.S. Application Data

(60) Provisional application No. 60/475,460, filed on Jun. 2, 2003.

(51) Int. Cl.
*C07H 21/00* (2006.01)
*C07H 21/02* (2006.01)
*C07H 21/04* (2006.01)
*C12Q 1/68* (2006.01)

(52) U.S. Cl. .................. 536/25.3; 536/23.1; 536/25.34; 435/6

(58) Field of Classification Search .............. 536/23.1, 536/25.3, 25.34; 435/6
See application file for complete search history.

(56) References Cited

U.S. PATENT DOCUMENTS

| | | | |
|---|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,458,732 A | 7/1984 | Yoshida et al. |
| 4,469,863 A | 9/1984 | Ts'o et al. |
| 4,500,707 A | 2/1985 | Caruthers et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,668,777 A | 5/1987 | Caruthers et al. |
| 4,725,677 A | 2/1988 | Koster et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,973,679 A | 11/1990 | Caruthers et al. |
| 4,981,957 A | 1/1991 | Lebleu et al. |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,124,047 A | 6/1992 | Quach et al. |
| 5,130,302 A | 7/1992 | Spielvogel et al. |
| 5,132,418 A | 7/1992 | Caruthers et al. |
| 5,134,066 A | 7/1992 | Rogers et al. |
| 5,138,045 A | 8/1992 | Cook et al. |
| RE34,069 E | 9/1992 | Koster et al. |
| 5,166,315 A | 11/1992 | Summerton et al. |
| 5,166,387 A | 11/1992 | Hirschbein |
| 5,175,273 A | 12/1992 | Bischofberger et al. |
| 5,185,444 A | 2/1993 | Summerton et al. |
| 5,212,295 A | 5/1993 | Cook |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,223,168 A | 6/1993 | Holt |
| 5,235,033 A | 8/1993 | Summerton et al. |
| 5,245,022 A | 9/1993 | Weis et al. |
| 5,254,469 A | 10/1993 | Warren, III et al. |

(Continued)

FOREIGN PATENT DOCUMENTS

EP           216860           10/1992

(Continued)

OTHER PUBLICATIONS

U.S. Appl. No. 10/155,920, filed May 24, 2002, Manoharan et al.

(Continued)

*Primary Examiner*—Jezia Riley
(74) *Attorney, Agent, or Firm*—Woodcock Washburn LLP

(57) ABSTRACT

The invention provides for methods of manufacturing an oligonucleotide comprising a pentavalent phosphate triester. In particular, the method comprises providing a 5' blocked-nucleoside, deblocking the 5' blocked-nucleoside to form a 5' OH-nucleoside, coupling the 5' OH-nucleoside with a phosphoramidite to form and oligonucleotide comprising a trivalent phosphite triester; and oxidizing the oligonucleotide comprising a trivalent phosphite triester to the oligonucleotide comprising a pentavalent phosphate triester. In some embodiments, the wash between any of the steps above is with at least one solvent wash comprising a toluene.

27 Claims, No Drawings

U.S. PATENT DOCUMENTS

| | | | |
|---|---|---|---|
| 5,258,506 A | 11/1993 | Urdea et al. |
| 5,262,536 A | 11/1993 | Hobbs, Jr. |
| 5,264,562 A | 11/1993 | Matteucci |
| 5,264,564 A | 11/1993 | Matteucci |
| 5,272,250 A | 12/1993 | Spielvogel et al. |
| 5,278,302 A | 1/1994 | Caruthers et al. |
| 5,292,863 A | 3/1994 | Wang |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,371,241 A | 12/1994 | Brush |
| 5,378,825 A | 1/1995 | Cook |
| 5,386,023 A | 1/1995 | Sanghvi et al. |
| 5,391,723 A | 2/1995 | Priest |
| 5,393,878 A | 2/1995 | Leumann |
| 5,405,938 A | 4/1995 | Summerton et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,455,233 A | 10/1995 | Spielvogel et al. |
| 5,457,187 A | 10/1995 | Gmeiner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,506,351 A | 4/1996 | McGee |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,521,302 A | 5/1996 | Cook |
| 5,525,465 A | 6/1996 | Haralambidis et al. |
| 5,525,711 A | 6/1996 | Hawkins et al. |
| 5,539,082 A | 7/1996 | Nielsen et al. |
| 5,541,307 A | 7/1996 | Cook et al. |
| 5,541,313 A | 7/1996 | Ruth |
| 5,545,730 A | 8/1996 | Urdea et al. |
| 5,552,538 A | 9/1996 | Urdea et al. |
| 5,552,540 A | 9/1996 | Haralambidis |
| 5,554,746 A | 9/1996 | Ravikumar et al. |
| 5,561,225 A | 10/1996 | Maddry et al. |
| 5,567,811 A | 10/1996 | Misiura et al. |
| 5,571,902 A | 11/1996 | Ravikumar et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook |
| 5,587,470 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,797 A | 2/1997 | Cook et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cooke |
| 5,700,920 A | 12/1997 | Altmann et al. |
| 5,714,331 A | 2/1998 | Buchardt et al. |
| 5,719,262 A | 2/1998 | Buchardt et al. |
| 5,750,692 A | 5/1998 | Cook et al. |
| 5,763,588 A | 6/1998 | Matteucci et al. |
| 5,792,608 A | 8/1998 | Swaminathan et al. |
| 5,817,781 A | 10/1998 | Swaminathan et al. |
| 5,830,653 A | 11/1998 | Froehler et al. |
| 5,859,221 A | 1/1999 | Cook et al. |
| 5,874,553 A | 2/1999 | Peyman et al. |
| 5,908,926 A * | 6/1999 | Pirrung et al. ............ 536/25.34 |
| 6,005,096 A | 12/1999 | Matteucci et al. |
| 6,007,992 A | 12/1999 | Lin et al. |
| 6,028,183 A | 2/2000 | Lin et al. |
| 6,127,346 A | 10/2000 | Peyman et al. |
| 6,147,200 A | 11/2000 | Manoharan et al. |
| 6,172,208 B1 | 1/2001 | Cook |
| 6,242,591 B1 | 6/2001 | Cole et al. |
| 6,262,241 B1 | 7/2001 | Cook et al. |
| 6,271,358 B1 | 8/2001 | Manoharan et al. |
| 6,465,625 B1 | 10/2002 | Dordick et al. |
| 6,576,752 B1 | 6/2003 | Manoharan et al. |
| 6,593,466 B1 | 7/2003 | Manoharan et al. |
| 6,639,062 B2 | 10/2003 | Manoharan et al. |

FOREIGN PATENT DOCUMENTS

| | | |
|---|---|---|
| WO | WO89/12060 | 12/1989 |
| WO | WO90/02749 | 3/1990 |
| WO | WO90/15065 | 12/1990 |
| WO | WO91/08213 | 6/1991 |
| WO | WO91/15500 | 10/1991 |
| WO | WO91/18997 | 12/1991 |
| WO | WO92/05186 | 4/1992 |
| WO | WO92/19637 | 11/1992 |
| WO | WO92/20822 | 11/1992 |
| WO | WO92/20823 | 11/1992 |
| WO | WO 00/08044 | 2/2000 |

OTHER PUBLICATIONS

U.S. Appl. No. 10/013,295, filed May 24, 2002, Manoharan et al.
U.S. Appl. No. 09/996,292, filed Nov. 28, 2001, Manoharan et al.
Altmann, K.-H. et al. "Second-generation antisense oligonucleotides: structure-activity relationships and the design of improved signal-transduction inhibitors," *Biochem Soc Trans.*, 1996,24(3):630-637.
Altmann, K.-H. et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides," *Nucleosides Nucleotides*, 1997, 16(7-9):917-926.

Altmann, K.-H. et al., "Second Generation of Antisense Oligonucleotides: From Nuclease Resistance to Biological Efficacy in Animals," *Chimia*, 1996, 50(4):168-176.

Altschul, S. F. et al., "Basic local alignment search tool," *J. Mol. Biol.*, 1990, 215(3):403-410.

Alul, R. H. et al., "Oxalyl-CPG: a labile support for synthesis of sensitive oligonucleotide derivatives," *Nucleic Acids Res.*, 1991,19(7):1527-1532.

Atherton, E. et al. "Polyamide supports for polypeptide synthesis," *J. Am. Chem. Soc.*, 1975, 97(22):6584-6585.

Baker, B. F. et al., "2'-O-(2-Methoxy)ethyl-modified Anti-intercellular Adhesion Molecule 1 (ICAM-1) Oligonucleotides Selectivity Increase the ICAM-1 mRNA Level and Inhibit Formation of the ICAM-1 Translation Initiation Complex in Human Umbilical Vein Endothelial Cells," *J. Biol. Chem.*, 1997, 272(18):11944-12000.

Bayer, E. et al., "A new support for polypeptide synthesis in columns," *Tetrahedron Lett.*, 1970, 51:4503-4505.

Beaucage, S. L., "Oligodeoxyribonucleotides synthesis. Phosphoramidite Approach," *Methods Mol Biol.*, 1993, 20:33-61.

Berg, R. H. et al., "Long-Chain Polysytrene-Grafted Polyethylene Film Matrix: A New Support for Solid-Phase Peptide Synthesis," *J. Am. Chem. Soc.*, 1989, 111:8024-8026.

Bonora, G. M. et al., "A Liquid-Phase Process Suitable for Large-Scale Synthesis of Phosphorothioate Oligonucleotides," *Organic Process Research & Development*, 2000, 4(3):225-231.

Braasch, D. A. et al., "Novel Antisense and Peptide Nucleic Acid Strategies for Controlling Gene Expression," *Biochem.*, 2002, 41(14):4503-45108.

Brazma, A. et al., "Gene expression data analysis," *FEBS Lett.*, 2000, 480(1):17-24.

Carulli, J. P. et al., "High throughput analysis of differential gene expression," *J. Cell. Biochem. Suppl.* 1998, 30-31:286-296.

Celis, J. E. et al., "Gene expression profiling: monitoring transcription and translation products using DNA microarrays and proteomics," *FEBS Lett.*, 2000, 480(1):2-16.

Conte, M. R. et al., "Conformational properties and thermodynamics of the RNA duplex r(CGCAAAUUUGCG)$_2$: comparison with the DNA analogue d(CGCAAATTTGCG)$_2$," *Nucleic Acids Res.*, 1997, 25(13):2627-2634.

Coull, J. M. et al., "Synthesis and Characterization of a Carbamate-Linked Oligonucleoside," *Tet. Lett.*, 1987, 28:745-748.

Crooke, S. T. et al., "Progress in antisense therapeutics," *Med Res Rev.* 1996,16(4):319-44.

Crooke, S. T. et al., "Pharmacokinetic properties of several novel oligonucleotide analogs in mice," *J. Pharmacol. Exp. Ther.*, 1996, 277(2):923-937.

Damha, M. J. et al., "Hybrids of RNA and Arabinonucleic Acids (ANA and 2'F-ANA) are Substrates of Ribonuclease H," *J. Am. Chem. Soc.*, 1998, 120(49):12976-12977.

Daniels, S. B. et al., "Membranes as Solid Supports for Peptide Synthesis," *Tetrahedron Lett*, 1989, 30(33):4345-4348.

De Mesmaeker, A. et al., "Antisense Oligonucleotides," *Acc. Chem. Res.*, 1995, 28(9):366-374.

Egli, M. et al., "RNA hydration: a detailed look," *Biochemistry*, 1996, 35(26):8489-8494.

Eichler, J. et al., "Application of Cellulose Paper as Support Material in Simultaneous Solid Phase Peptide Synthesis," *Collect. Czech. Chem. Commun.*, 1989, 54:1746-1752.

Englisch, U. et al., "Chemically Modified Oligonucleotides as Probes and Inhibitors," *Angewandte Chemie*, 1991, 30(6):613-722.

Fedoroff, O. Y. et al., "Structure of a DNA:RNA Hybrid Duplex Why RNase H Does Not Cleave Pure RNA," *J. Mol. Biol.*, 1993, 233:509-523.

Flanagan, W. M. et al., "A cytosine analog that confers enhanced potency to antisense oligonucleotides," *Proc. Natl. Acad. Sci. USA*, 1999, 96(7):3513-3518.

Freier, S. M. et al., "The ups and downs of nucleic acid duplex stability: structure-stability studies on chemically-modified DNA:RNA duplexes," *Nucleic Acids Res.*, 1997; 25(22):4429-4443.

Froehler, B. C. "Oligodeoxynucleotide synthesis. H-phosphonate approach," *Methods Mol Biol.*, 1993, 20:63-80.

Fuchs, B. et al., "Identification of differentially expressed genes by mutually subtracted RNA fingerprinting," *Anal. Biochem.* 2000, 286(1):91-98.

Gait, M. J., "Oligoribonucleotides," *Antisense Research and Applications*, S. T. Crooke and L. Bernard (eds.), CRC Press, Inc., Boca Raton, 1993, pp. 289-301.

Geysen, H. M. et al., "Use of peptide synthesis to probe viral antigens for epitopes to a resolution of a single amino acid," *Proc. Natl. Acad. Sci. USA*, 1984, 81(13):3998-4002.

Going, J. J. et al., "Molecular pathology and future developments," *Eur. J. Cancer*, 1999, 35(14):1895-1904.

Gonzalez, C. et al., "Structure and dynamics of a DNA-RNA hybrid duplex with a chiral phosphorothioate moiety: NMR and molecular dynamics with conventional and time-averaged restraints," *Biochemistry*, 1995, 34(15):4969-4982.

Gorman, J. J., "An apparatus for simultaneous manual solid-phase synthesis of multiple peptide analogs," *Anal. Biochem.*, 1984, 136(2):397-406.

Gravert, D. J. et al., "Organic Synthesis on Soluble Polymer Supports: Liquid-Phase Methodologies," *Chem. Rev.*, 1997, 97(2):489-510.

Hewitt, J. M. et al., "Structural Determination of Silicon-Containing Oligonucleotides by $^1$H-$^{29}$Si Long-Range Heteronuclear Multiple Quantum Correlation NMR Spectroscopy," *Nucleic Acid Res.*, 1992, 11(9):1661-1666.

Holm, A. et al., "Multiple Column Peptide Synthesis," *Proceedings Of The 20$^{th}$ European Peptide Symposium*, 1989, pp. 208-210.

Horn, T. et al., "Forks and combs and DNA: the synthesis of branched oligodeoxyribonucleotides," *Nucleic Acids Res.*, 1989, 17(17):6959-6967.

Horton, N. C. et al., "The structure of an RNA/DNA hybrid: a substrate of the ribonuclease activity of HIV-1 reverse transcriptase," *J. Mol. Biol.*, 1996, 264(3):521-533.

Houghten, R. A., "General method for the rapid solid-phase synthesis of large numbers of peptides: specificity of antigen-antibody interaction at the level of individual amino acids," *Proc. Natl. Acad. Sci. USA*, 1985, 82(15):5131-5135.

Jungblut, P. R. et al., "Proteomics in human disease: cancer, heart and infectious diseases," *Electrophoresis*, 1999, 20(10):2100-2110.

Jurecic, R. et al., "Long-distance DD-PCR and cDNA microarrays," *Curr. Opin. Microbiol.*, 2000, 3(3):316-321.

Kabanov, A. V. et al., "A new class of antivirals: antisense oligonucleotides combined with a hydrophobic substituent effectively inhibit influenza virus reproduction and synthesis of virus-specific proteins in MDCK cells," *FEBS Lett.*, 1990, 259(2):327-330.

Kent, S. B. H. et al., "Preparation and Properties of tert-Butyloxycarbonylaminoacyl-4-(oxymethyl) phenylacetamidomethyl-(Kel F-g-styrene) Resin, an Insoluble, Noncrosslinked Support for Solid Phase Peptide Synthesis," *Israel J. Chem.*, 1978, 17:243-247.

Krchnak, V. et al., "Multiple continuous-flow solid-phase peptide synthesis. Synthesis of an HIV antigenic peptide and its omission analogues," *Int. J. Pept. Protein Res.*, 1989, 33(3):209-213.

Kurchavov, N. A. et al., "A New Phosphoramidite Reagent for the Incorporation of Diazaphenoxazinone Nucleoside with Enhanced Base-Pairing Properties into Oligodeoxynucleotides," *Nucleosides & Nucleotides*, 1997, 16(10&11):1837-1846.

Lane, A. N. et al., "NMR assignments and solution conformation of the DNA•RNA hybrid duplex d(GTGAACTT)•r(AAGUUCAC)," *Eur. J. Biochem.*, 1993, 215(2):297-306.

Larson, E. J. et al., "Rapid DNA fingerprinting of pathogens by flow cytometry," *Cytometry*, 2000, 41(3):203-208.

Larsson, M. et al., "High-throughput protein expression of cDNA products as a tool in functional genomics," *J. Biotechnol.*, 2000, 80(2):143-157.

Lebl M. et al., "Simulation of Continuous Solid Phase Synthesis: Synthesis of Methionine Enkephalin and its Analogs," *Peptide Res.*, 1989, 2(4):297-300.

Lesnik, E. A. et al., "Relative thermodynamic stability of DNA, RNA, and DNA:RNA hybrid duplexes: relationship with base composition and structure," *Biochemistry*, 1995, 34(34):10807-10815.

Letsinger, R. L. et al., "Cholesteryl-conjugated oligonucleotides: synthesis, properties, and activity as inhibitors of replication of human immunodeficiency virus in cell culture," *Proc. Natl. Acad. Sci. USA.*, 1989, 86(17):6553-6556.

Lin, K.-Y. et al., "Tricyclic 2'-Deoxycytidine Analogs: Syntheses and Incorporation into Oligodeyxonucleotides Which Have Enhanced Binding to Complementary RNA," *J. Am. Chem. Soc.*, 1995, 117(13):3873-3874.

Lin, K.-Y. et al., "A Cytosine Analogue Capable of Clamp-Like Binding to a Guanine in Helical Nucleic Acids," *J. Am. Chem. Soc.*, 1998, 120(33):8531-8532.

Madden, S. L. et al., "Serial analysis of gene expression: from gene discovery to target identification ," *Drug Discov. Today*, 2000, 5(9):415-425.

Manoharan, M. et al., "Cholic Acid-Oligonucleotide Conjugates for Antisense Applications," *Bioorg. Med. Chem. Lett.*, 1994, 4(8):1053-1060.

Manoharan, M. et al., "Chemical modifications to improve uptake and bioavailability of antisense oligonucleotides," *Ann N Y Acad Sci.*, 1992, 660:306-309.

Manoharan, M. et al., "Introduction of a Lipophilic Thioether Tether in the Minor Groove of Nucleic Acids for Antisense Applications," *Bioorg. Med. Chem. Let.*, 1993, 3(12):2765-2770.

Manoharan, M. et al., "Lipidic Nucleic Acids," *Tetrahedron Lett.*, 1995, 36(21):3651-3654.

Manoharan, M. et al., "Oligonucleotide Conjugates: Alteration of the Pharmacokinetic Properties of Antisense Agents," *Nucleosides & Nucletides*, 1995, 14(3-5):969-973.

Martin, P., "Ein neuer Zugang zu 2'-O-Alkylribonucleosiden und Eigenschaften deren Oligonucleotide," *Helv. Chim. Acta*, 1995, 78:486-504.

Mertes, M. P. et al., "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate," *J. Med. Chem.*, 1969, 12(1):154-157.

Mishra, R. K. et al., "Improved leishmanicidal effect of phosphorotioate antisense oligonucleotides by LDL-mediated delivery," *Biochim. Biophys. Acta.*, 1995, 1264(2):229-237.

Mungall, W. S. et al., "Carbamate analogues of oligonucleotides," *J. Org. Chem.*, 1977, 42(4):703-706.

Musicki, B. et al., "Synthesis of Carbohydrate Sulfonates and Sulfonate Esters," *J. Org. Chem.*, 1990, 55(14):4231-4233.

Nielsen, P. E. et al., "Sequence-selective recognition of DNA by strand displacement with a thymine-substituted polyamide," *Science*, 1991, 254(5037):1497-1500.

Oberhauser, B. et al., "Effective incorporation of 2'-O-methyl-oligoribonucleotides into liposomes and enhanced cell association through modification with thiocholesterol," *Nucleic Acids Res.*, 1992, 20(3):533-538.

Parr, W. et al., "Solid-phase peptide synthesis on an inorganic matrix having organic groups on the surface," *Angew. Chem. Int. Ed. Engl.*, 1972, 11(4):314-315.

Prashar, Y. et al., "READS: a method for display of 3'-end fragments of restriction enzyme-digested cDNAs for analysis of differential gene expression," *Methods in Enzymol.*, 1999, 303:258-272.

Reese, C. B., "The Chemical Synthesis of Oligo- and Polynucleotides by the Phosphotriester Approach," *Tetrahedron*, 1978, 34:3143-3179.

Reynolds, R. C. et al., "Synthesis of Thymidine Dimers Containing Internucleoside Sulfonate and Sulfonamide Linkates," *J. Org. Chem.*, 1992, 57(11):2983-2985.

Saison-Behmoaras, T. et al., "Short modified antisense oligonucleotides directed against Ha-*ras* point mutation induce selective cleavage of the mRNA and inhibit T24 cells proliferation," *EMBO J.*, 1991,10(5):1111-1118.

Sanger et al., *Principles Of Nucleic Acid Structure*, 1984.

Sanghvi, Y. S., "Heterocyclic Base Modifications in Nucleic Acids and Their Applications in Antisense Oligonucleotides," *Antisense Research And Applications*, S. T. Crooke and L. Bernard (eds.), CRC Press, Inc., Boca Raton, 1993, pp. 276-288.

Scott, R. P. W. et al., "The Use of Resin Coated Glass Beads in the Form of a Packed Bed for the Solid Phase Synthesis of Peptides," *J. Chrom. Sci*, 1971, 9:577-591.

Searle, M. et al., "On the stability of nucleic acid structures in solution: enthalpy-entropy compensations, internal rotations and reversibility," *Nucleic Acids Res.*, 1993, 21(9):2051-2056.

Shea, R. G. et al., "Synthesis, hybridization properties and antiviral activity of lipid-oligodeoxynucleotide conjugates," *Nucleic Acids Res.*, 1990, 18(13):3777-3783.

Singh, S. K. et al., "LNA (locked nucleic acids): synthesis and high-affinity nucleic acid recognition," *Chem. Commun.*, 1998, 4:455-456.

Sood, A. et al., "Boron-Containing Nucleic Acids. 2. Synthesis of Oligodeoxynucleoside Boranophosphates," *J. Am. Chem. Soc.*, 1990, 112: 9000-9001.

Stirchak, E. P. et al., "Uncharged Steroregular Nucleic Acid Analogues. 1. Synthesis of a Cytosine-Containing Oligomer with Carbamate Internucleoside Linkages," *J. Org. Chem.*, 1987, 52(19):4202-4206.

Stirchak, E. P. et al., "Uncharged steroregulator nucleic acid analogs: 2. Morpholino nucleoside oligomers with carbamate internucleoside linkages," *Nucleic Acids Res.*, 1989, 17(15):6129-6141.

Sutcliffe, J. G. et al., "TOGA: an automated parsing technology for analyzing expression of nearly all genes," *Proc. Natl. Acad. Sci. USA*, 2000, 97(5):1976-1981.

Svinarchuk, F. P. et al., "Inhibition of HIV proliferation in MT-4 cells by antisense oligonucleotide conjugated to lipophilic groups," *Biochimie*, 1993, 75(1-2):49-54.

To, K.-Y., "Identification of differential gene expression by high throughput analysis," *Comb. Chem. High Throughput Screen.*, 2000, 3(3):235-241.

Tregear, G. W., "Graft Copolymers as Insoluble Supports in Peptide Synthesis," *Chemistry And Biology Of Peptides*, 1972, pp. 175-178.

Van Rietschoten, J. et al., "Simultaneous Synthesis of Two Peptide Analogs on Different Insoluble Supports," *Pept., Proc. Eur. Pept. Symp., 13th*, 1975, pp. 113-116.

Vasseur, J.-J. et al., "Oligonucleosides: Synthesis of a Novel Methylhydroxylamine-Linked Nucleoside Dimer and Its Incorporation into Antisense Sequences," *J. Amer. Chem. Soc.*, 1992, 114:4006-4007.

Vester, B. et al., "LNAzymes: incorporation of LNA-type monomers into DNAzymes markedly increases RNA cleavage," *J. Am. Chem. Soc.*, 2002, 24(46):13682-13683.

Wang, H. et al., "Solid Phase Synthesis of Neutral Oligonucleotide Analogues," *Tet. Lett.*, 1991, 32(50):7385-7388.

Wang, J. et al., "Cyclohexane Nucleic Acids (CeNa): Serum Stable Oligonucleotides that Activate RNase H and Increase Duplex Stability with Complementary RNA," *J. Am. Chem. Soc.*, 2000, 122(36):8595-8602.

Wang, J. et al., "Synthesis and binding property of an oligonucleotide containing tetrafluorophenoxazine," *Tetrahedron Lett.*, 1998, 39:8385-8388.

Wilds, C. J. et al., "Duplex recognition by oligonucleotides containing 2'-deoxy-2'-fluoro-D-arabinose and 2'-deoxy-2'-fluoro-D-ribose. Intermolecular 2'-OH-phosphate contacts versus sugar puckering in the stabilization of triple-helical complexes," *Bioconjug. Chem.*, 1999,10(2):299-305.

Wright, P. et al., "Large Scale Synthesis of Oligonucleotides via Phosphoramidite Nucleosides and a High-loaded Polystyrene Support," *Tetrahedron Letters*, 1993, 34(21):3373-3376.

Zhang, J. et al., "PowerBLAST: a new network BLAST application for interactive or automated sequence analysis and annotation," *Genome Res.*, 1997, 7(6):649-656.

Atkinson, T. et al., "Solid-phase Synthesis of Oligodeoxyribonucleotides by the Phosphitetriester Method." *Oligonucleotide synthesis: a practical approach*, M. J. Gait (ed.), IRL Press, New York, 1984, pp. 51-52.

"Preparaing the system for a run," *ÄKTA oligopilot Making Your First Run*, Amersham Biosciences, 2000, p. 7.

Atkinson et al., "Oligonucleotide Synthesis, A practical approach," M.J. Gait (Editor), IRL Press, New York, (1984) pp. 51-52.

International Search Report dated Apr. 25, 2005 for International Application No. PCT/US04/17083.

* cited by examiner

OLIGONUCLEOTIDE SYNTHESIS WITH ALTERNATIVE SOLVENTS

CROSS REFERENCE TO RELATED APPLICATION

This application claims the benefit of U.S. Provisional Application No. 60/475,460 filed Jun. 2, 2003. The entire disclosure of this application is incorporated herein by reference

FIELD OF THE INVENTION

The present invention is directed to the field of oligomer synthesis. In particular, the present invention concerns improved oligomer synthesis using solvents other than acetonitrile.

BACKGROUND OF THE INVENTION

Proteins, acting directly or through their enzymatic functions, contribute in major proportion to many diseases in animals and humans. Classical therapeutic methods have generally focused on modulating protein function with exogenous compounds that interact directly with proteins, with the goal of moderating their disease-causing or disease-potentiating functions. Recently, however, attempts have been made to affect the production of certain proteins by modulating the activity of molecules that direct protein synthesis, such as intracellular RNA. By interfering with the production of specific proteins, it has been hoped to effect therapeutic results with maximal desired effect and minimal side effects.

One method for inhibiting specific gene expression involves using oligonucleotides or oligonucleotide analogs as "antisense" agents. Antisense technology involves directing oligonucleotides, or analogs thereof, to a specific, target messenger RNA (mRNA) sequence. The interaction of exogenous "antisense" molecules and endogenous mRNA modulates transcription by a variety of pathways. Such pathways include transcription arrest, RNAse H recruitment, and RNAi (e.g. siRNA). Antisense technology permits modulation of specific protein activity in a relatively predictable manner.

In fact, antisense oligonucleotides and oligonucleotide analogs are now accepted as therapeutic agents that hold great promise for therapeutic and diagnostic methods. Accordingly, it has become desirable to produce oligonucleotides and their analogs in relatively large quantities. In some applications, it is necessary to produce large numbers of small batches of diverse oligonucleotides or their analogs for screening purposes. In other cases, for example in the production of therapeutic quantities of oligonucleotides and their analogs, it is necessary to make large batches of the same oligonucleotide, or analog thereof.

Three principal methods have been used for the synthesis of oligonucleotides. The phosphotriester method, as described by Reese, *Tetrahedron* 1978, 34, 3143; the phosphoramidite method, as described by Beaucage, in *Methods in Molecular Biology: Protocols for Oligonucleotides and Analogs*; Agrawal, ed.; Humana Press: Totowa, 1993, Vol. 20, 33-61; and the H-phosphonate method, as described by Froehler in *Methods in Molecular Biology: Protocols for Oligonucleotides and Analogs* Agrawal, ed.; Humana Press: Totowa, 1993, Vol. 20, 63-80. Of these three methods, the phosphoramidite method has become a defacto standard in the industry.

A typical oligonucleotide synthesis using phosphoramidite chemistry (i.e. the amidite methodology) is set forth below. First, a primer support is provided in a standard synthesizer column. The primer support is typically a solid support (supt) having a linker (link) covalently bonded thereto. It is common to purchase the primer support with a first 5'-protected nucleoside bonded thereto.

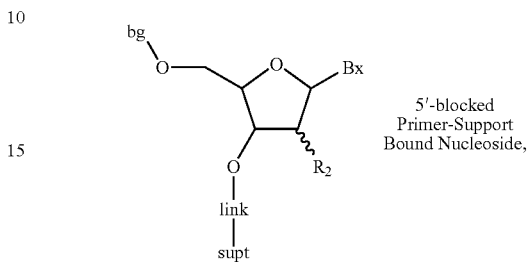

5'-blocked Primer-Support Bound Nucleoside, wherein bg is a 5'-blocking group, Bx is a nucleobase, $R_2$ is H, OH, OH protected with a removable protecting group, or a 2'-substituent, such as 2'-deoxy-2'-methoxyethoxy (2'-MOE), link is the covalent linking group, which joins the nucleoside to the support, supt.

(A) The 5'-blocking group bg (e.g. 4,4'-dimethoxytrityl) is first removed (e.g. by exposing the 5'-blocked primer-support bound nucleoside to an acid, thereby producing a support-bound nucleoside of the formula:

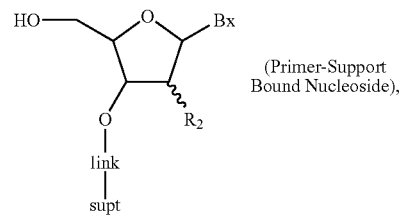

(Primer-Support Bound Nucleoside), wherein supt is the solid support, link is the linking group, Bx is a nucleobase, $R_2$ is H, OH, OH protected with a removable protecting group, or a 2'-substituent.

(B) The column is then washed with acetonitrile, which acts to both "push" the regent (acid) onto the column, and to wash unreacted reagent and the removed 5'-blocking group (e.g. trityl alcohol) from the column.

(C) The primer support is then reacted with a phosphitylation reagent (amidite), which is dissolved in acetonitrile, the amidite having the formula:

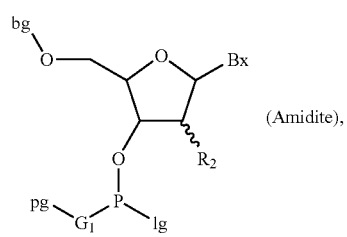

(Amidite), wherein bg is a 5'-blocking group, lg is a leaving group, $G_1$ is O or S, pg is a phosphorus protecting group, and $R_2$ and Bx have, independent of the analogous variables on the primer support, the same definitions as previously defined.

The product of this reaction is the support-bound phosphite dimer:

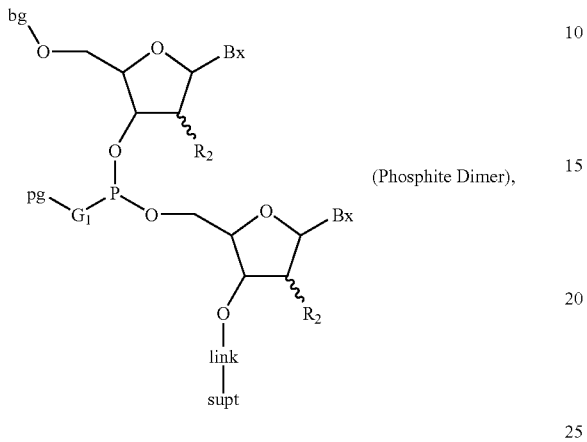

(Phosphite Dimer), wherein each of the variables bg, $G_1$, pg, $R_2$ and Bx is independently defined above, link is the linker and supt is the support, as defined above.

(D) The support-bound dimer is then typically washed with acetonitrile.

(E) The support-bound dimer is then typically reacted with an oxidizing agent, such as a thiating agent (e.g. phenylacetyl disulfide), in acetonitrile, to form a support-bound phosphate triester:

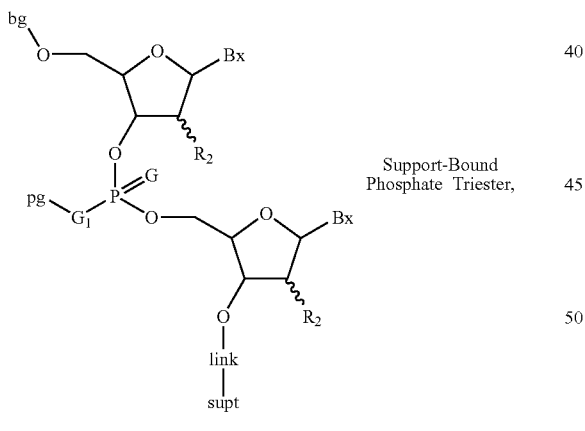

Support-Bound Phosphate Triester, wherein each of G and $G_1$ is, independently, O or S and the other variables are defined herein.

(F) The column is then washed again with acetonitrile.

(G) A capping reagent in acetonitrile is then added to the column, thereby capping unreacted nucleoside.

(H) The support-bound phosphate triester is then typically washed with acetonitrile.

Steps (A)-(H) are then repeated, if inecessary, a sufficient number of times (n−1) to prepare a support-bound, blocked oligonucleotide having the formula:

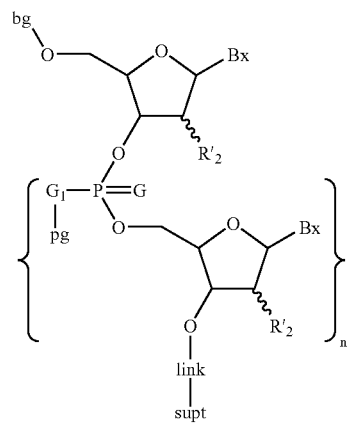

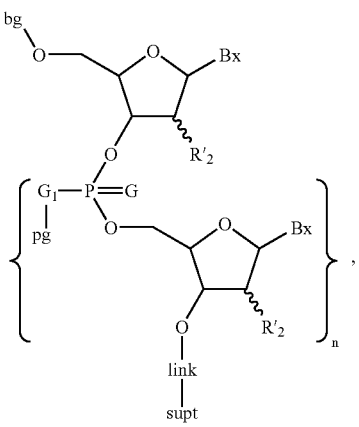

wherein n is a positive integer (typically about 7 to about 79).

The phosphorus protecting groups pg are then typically removed from the oligomer to produce a support-bound oligomer having the formula:

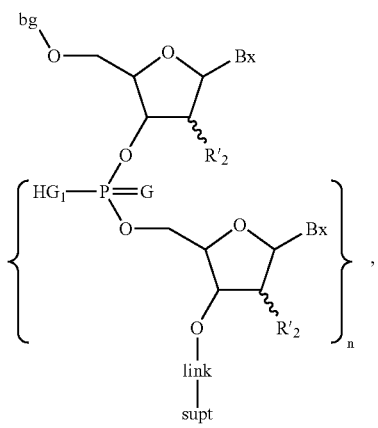

which, after washing with a suitable solvent wash, such as acetonitrile, is typically cleaved from the solid support, purified, 5'-deblocked, and further processed to produce an oligomer of the formula:

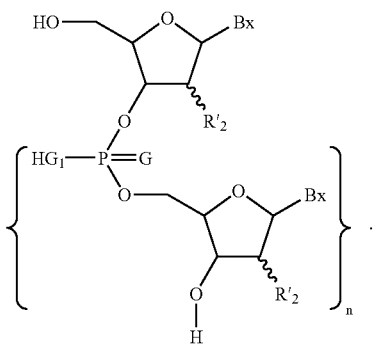

The foregoing methodology has historically proven effective in the production of small- to medium-scale quantities of oligonucleotide. In fact, heretofore it has been believed that acetonitrile is the best solvent for use in oligonucleotide synthesis, including dissolution and introduction of reagents to the column, as well as for column washing steps between reagent addition steps. It has been believed, in fact, that the polarity, viscosity and other characteristics of acetonitrile made it the solvent of choice for solid phase oligonucleotide synthesis. However, acetonitrile is a relatively expensive solvent. If acetonitrile could be replaced with a less-costly solvent, it could potentially produce extensive cost savings, especially as the scale of oligonucleotide synthesis increases. Nevertheless, the long-held belief in the art was that acetonitrile could not be replaced as a solvent without sacrificing oligonucleotide purity or yield, either one of which would be unacceptable in view of the high cost of raw materials such as amidites.

There is therefore a need for a substitute for acetonitrile as a solvent in oligonucleotide synthesis.

There is also a need for a substitute solvent wash for oligonucleotide synthesis.

There is also a need for a reagent push other than acetonitrile for use in oligonucleotide synthesis.

There is also a need for an oligonucleotide synthetic method using an alternative solvent wash that supports production of oligonucleotides in purity at least as good as acetonitrile.

There is also a need for an oligonucleotide synthetic method using an alternative solvent wash that supports production of oligonucleotides in yields at least as good as those supported by acetonitrile.

There is also a need for an oligonucleotide synthetic method using an alternative solvent wash that is less expensive than acetonitrile.

SUMMARY OF THE INVENTION

The foregoing and other needs are met by embodiments of the present invention. For example, the acetonitrile that is customarily used as a washing solvent in the synthesis process is entirely or partly replaced with an alternative solvent in at least one wash step.

In some embodiments, the present invention provides methods of synthesizing/manufacturing an oligonucleotide that comprises a pentavalent phosphate triester. In some embodiments, the method comprises the step of providing a 5' blocked-nucleoside, deblocking the 5' blocked-nucleoside to form a 5' OH-nucleoside, coupling the 5' OH-nucleoside with a phosphoramidite to form an oligonucleotide comprising a trivalent phosphite triester, and oxidizing the oligonucleotide comprising a trivalent phosphite triester to the oligonucleotide comprising a pentavalent phosphate triester. In some embodiments, one or more of the steps above is followed by a wash with a solvent wash. In some embodiments, the solvent wash that is used in one or more of the washes comprises, for example, toluene, pyridine, lutidine, hexane, cyclohexane, cyclohexene, a halogenated benzene, alkylated benzenes, a haloalkylbenzene, acetone, ethylacetate, methanol, ethanol, phenol, cyclic ethers, acyclic ethers, halogenated alkanes or mixtures thereof. In some embodiments, the solvent wash comprises a toluene and an acetonitrile. In some embodiments, the solvent wash is substantially free of an acetonitrile. As used herein, a solvent wash is substantially free of an acetonitrile is a solvent comprising less than about 1% of acetonitrile.

In some embodiments, the 5' blocked-nucleoside is linked to another nucleoside. In some embodiments, the 5' blocked-nucleoside is linked to a solid support, for example a controlled pore glass (CPG) which consists of a glass matrix prepared uniformly with pores of defined size. In some embodiments, the 5' blocked-nucleoside comprises a sugar moiety and a base.

One advantage of the present invention is that it provides method of solid phase oligonucleotide synthesis in which a detritylation step is followed by a wash step, the wash step employing toluene or some other solvent, other than acetonitrile.

Another advantage of the present invention is that it provides a method of solid phase oligonucleotide synthesis in which an oxidation step, in particular a sulfurization step, is followed by a wash step in which the solvent is other than acetonitrile, such as toluene.

Another advantage of the present invention is that it provides a method of solid phase oligonucleotide synthesis in which a capping step, in particular a sulfurization step, is followed by a wash step in which the solvent is other than acetonitrile, such as toluene.

Another aspect of the present invention is that it provides for washing of a solid phase of a solid phase oligonucleotide synthesis platform with at least one support volume of a solvent wash other than acetonitrile.

Other aspects and advantages of the present invention will become apparent to the person having skill in the art upon consideration of the following description of the invention, drawings and claims.

DESCRIPTION OF THE EMBODIMENTS

The present invention is partly based on the discovery that partially or totally replacing the acetonitrile with other solvent washes can provide for effective synthesis of oligonucleotides. For example, such replacement can result in acceptable removal of active compounds, such as reagents, by-products and activators, from a solid phase synthesis support.

In some embodiments, the present invention provides for a method of manufacturing an oligonucleotide comprising a pentavalent phosphate triester. In some embodiments, the method comprises the step of providing a 5' blocked-nucleoside, deblocking the 5' blocked-nucleoside to form a 5' OH-nucleoside, coupling the 5' OH-nucleoside with a phosphoramidite to form an oligonucleotide comprising a trivalent phosphite triester, and oxidizing the oligonucleotide comprising a trivalent phosphite triester to the oligonucleotide comprising a pentavalent phosphate triester.

In some embodiments, one or more of the steps above is followed by a wash with a solvent wash of the present invention.

In some embodiments, the solvent wash comprises only part or no acetonitrile. In some embodiments, all the washes are performed with a solvent wash that comprises only part or no acetonitrile. In some embodiments, some of the washes are performed with a solvent wash that comprises only part or no acetonitrile, and other washes are performed with acetonitrile.

Non-limiting examples of solvents that may be used independently or in a mixture with acetonitrile include toluene, pyridine, lutidine hexane, cyclohexane, cyclohexene, a halogenated benzene, such as chlorobenzene, other alkylated benzenes, e.g. p-xylene, m-xylene, o-xylene, and trimethylbenzene, a haloalkylbenzene, acetone, ethylacetate or an alcohol, such as methanol, ethanol, phenol, cyclic ethers, acyclic ethers, and halogenated alkanes, such as trichloroethylene.

In some embodiments, the solvent wash comprises about more than 70% toluene. In some embodiments, the solvent wash comprises about more than 50% toluene. In some embodiments, the solvent wash comprises about more than 30% toluene. In some embodiments, the solvent wash comprises about more than 10% toluene.

In some embodiments, the solvent wash comprises a toluene and an acetonitrile. In some embodiments, the solvent wash is substantially free of an acetonitrile. As used herein, a solvent wash is substantially free of an acetonitrile is a solvent comprising less than about 1% of acetonitrile.

In some embodiments, the solvent wash comprises about 50% (v/v) of non-acetonitrile solvents, the remaining 50% (v/v) being acetonitrile. In certain embodiments, the solvent wash other than acetonitrile consists of two or more solvents other than acetonitrile. In some embodiments, the solvent wash of the present invention comprises toluene, pyridine, lutidine, or a mixture of two or more thereof. The artisan will understand that the composition of the solvent wash is determined prior to its application to the solid support (for purposes of washing the solid support, pushing reagent onto or through the support, etc.), as the solvent's composition after it is applied to the support will change depending upon the composition of the solutions that have been applied to the support prior to the wash step.

In some embodiments, the step of deblocking the 5' blocked-nucleoside to form a 5' OH-nucleoside is followed by a wash with a solvent wash. In some embodiments, this wash is with a solvent wherein the acetonitrile is partially or totally replaced, for example with toluene.

In some embodiments, the step of coupling the 5' OH-nucleoside with a phosphoramidite to form and oligonucleotide comprising a trivalent phosphite trimester is followed by a wash with a solvent wash. In some embodiments, this wash is with a solvent wherein the acetonitrile is partially or totally replaced, for example with toluene.

In some embodiments, the step of oxidizing the oligonucleotide comprising a trivalent phosphite triester to the oligonucleotide comprising a pentavalent phosphate trimester is followed by a wash with a solvent wash. In some embodiments, this wash is with a solvent wherein the acetonitrile is partially or totally replaced, for example with toluene.

In some embodiments, the 5' blocked-nucleoside is linked to another nucleoside. In some embodiments, the 5' blocked-nucleoside is linked to a solid support, for example a controlled pore glass (CPG) which consists of a glass matrix prepared uniformly with pores of defined size. In some embodiments, the 5' blocked-nucleoside comprises a sugar and a base. In some embodiments, the sugar is a sugar ring or a modified sugar ring. Sugar rings include ribosyl, 2'-deoxyribosyl, arabinosyl, erythrosyl and other sugar rings. Modified sugar rings include the foregoing sugar rings as modified per the description herein, e.g. at the 2'-position, or by a bridge between the 2'- and 4'-positions as described in further detail herein. In some embodiments, a base is a purine, pyrimidine or modifications thereof.

In some embodiments, the invention features a method of manufacturing a compound of Formula I:

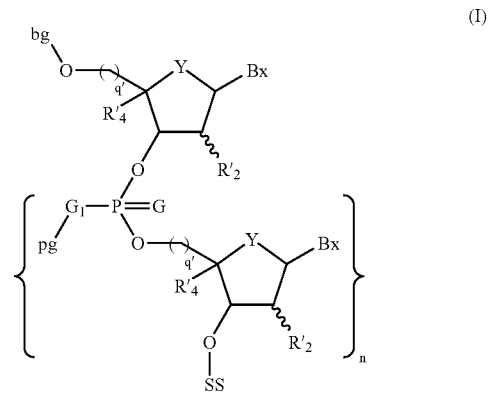

(I)

wherein Y is O, S, $CH_2$, CHF, $CF_2$ or —CH=CH—;

bg is a 5'-blocking group;

n is a positive integer;

each $R'_2$ is, independently, H, OZ, a 2'-substituent, or together with $R'_4$ forms a bridge;

each $R'_4$ is, independently, H, OZ, a 2'-substituent, or together with $R'_2$ forms a bridge;

Z is H or a removable protecting group each Bx is independently a nucleobase;

each pg is independently a phosphorus protecting group;

each G is O or S;

each $G_1$ is O or S;

each q' is independently 0 or 1; and

SS is a solid support.

In some embodiments, each Y is O. In some embodiments, n is about 7 to about 79. In some embodiment, each $R'_2$ is H or a 2'-substituent. In some embodiment, each $R'_2$ is H or a 2'-substituent, said 2'-substituent being a member of the group consisting of 2'-O—$CH_3$, 2'-O—$CH_2CH_2OCH_3$, or 2'-O—$(CH_2)_3NH_2$. In some embodiment, the 2'-substituent is 2'-$OCH_2CH_2OCH_3$. In some embodiment, each q' is 1. In some embodiment, each G is S.

In some embodiments, the method comprises:
(a) contacting a compound of Formula II:

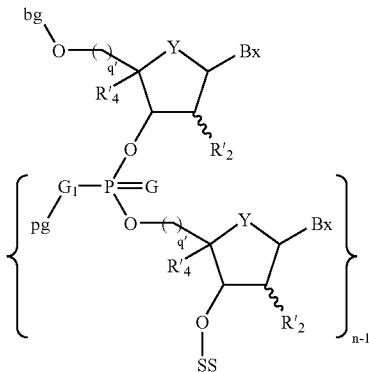

(II)

with a deblocking agent to produce a compound of Formula III:

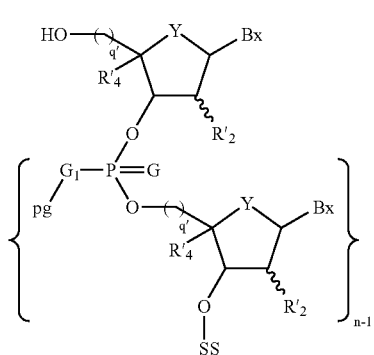

(III)

(b) contacting the compound of Formula III with a first solvent wash;
(c) contacting the compound of Formula III with a compound of Formula IV:

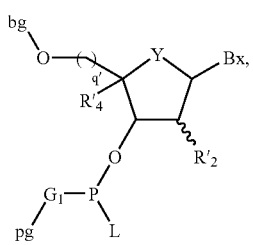

(IV)

wherein L is a leaving group (e.g., an amine such as a diisopropylamino group), to form a compound of Formula V:

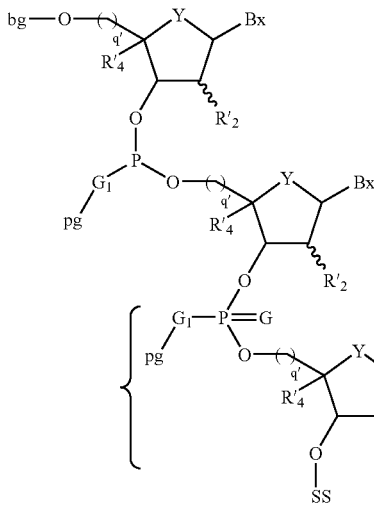

(V)

(d) contacting the compound of Formula V with a second solvent wash; and
(e) contacting the compound of Formula V with an oxidation reagent to form the compound of Formula I;

wherein at least one of the first and second solvent washes comprises a toluene.

In some embodiments, the first solvent wash comprises a toluene, for example, about more than 50% toluene. In some embodiments, the first solvent wash comprises the toluene and an acetonitrile. In some embodiments, the first solvent wash is substantially free of an acetonitrile.

In some embodiments, the second solvent wash comprises a toluene. In some embodiments, the second solvent wash comprises the toluene and an acetonitrile. In some embodiments, the second solvent wash is substantially free of an acetonitrile.

In some embodiments, after the oxidizing step (e), the compound of Formula I is washed with a third solvent wash. In some embodiments, the third solvent wash may comprise a toluene.

Since the coupling reaction cannot be quantitative in a finite time period, a small percentage of truncated sequences is produced at every coupling step. If these failure sequences were allowed to react further, it would be difficult to isolate the product from the sequence mixture. This problem may be overcome largely by capping the remaining free hydroxyls through acetylation. In some embodiments, the oxidizing step is immediately followed by a capping step.

In some embodiment, the compound of Formula I is cleaved from the solid support to form a compound of Formula X:

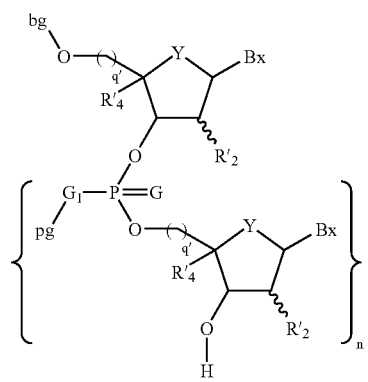

(X)

wherein the variables have the same definitions as described above.

In some embodiments, the present invention provides method of synthesizing an phosphorus-protected oligonucleotide having the formula I on a solid support:

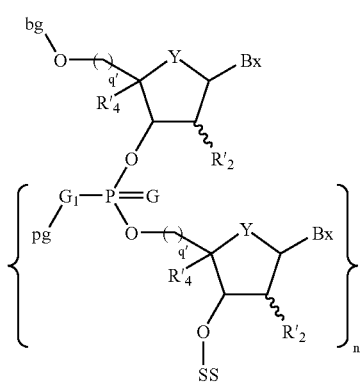
(I)

wherein Y is O, S, $CH_2$, CHF, $CF_2$ or —CH=CH—;
bg is a 5'-blocking group;
n is a positive integer;
each $R'_2$ is, independently, H, OH, OZ (wherein Z is a removable protecting group), a 2'-substituent, or together with $R'_4$ forms a bridge;
each $R'_4$ is, independently, H or together with $R'_2$ forms a bridge;
each Bx is independently a nucleobase;
each pg is independently a phosphorus protecting group;
each G is O or S;
each $G_1$ is O or S;
each q' is independently 0 or 1; and
SS is a solid support; said process comprising:
contacting a support-bound synthon II:

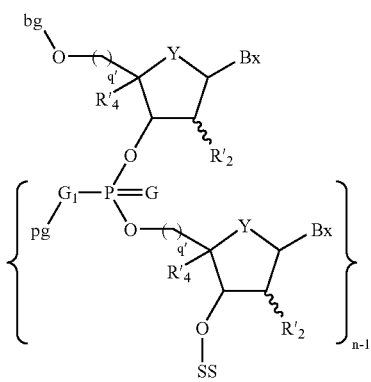
(II)

with a deblocking agent to produce a deprotected synthon III:

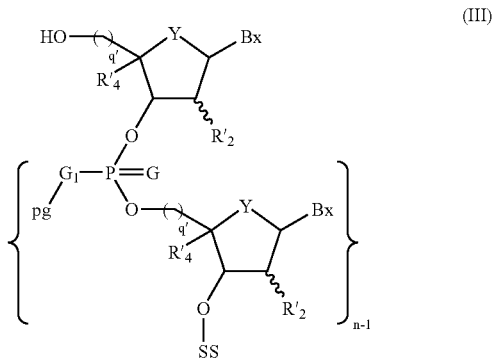
(III)

washing III with a first wash solvent;
contacting III with a phosphoramidite of formula IV:

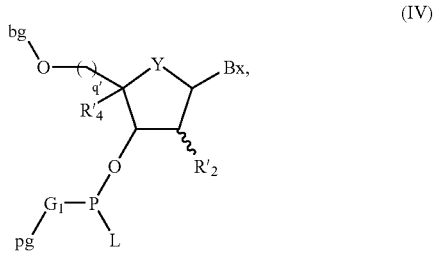
(IV)

wherein L is a leaving group, and the other variables are as in formula I to form a phosphitylated intermediate of formula V:

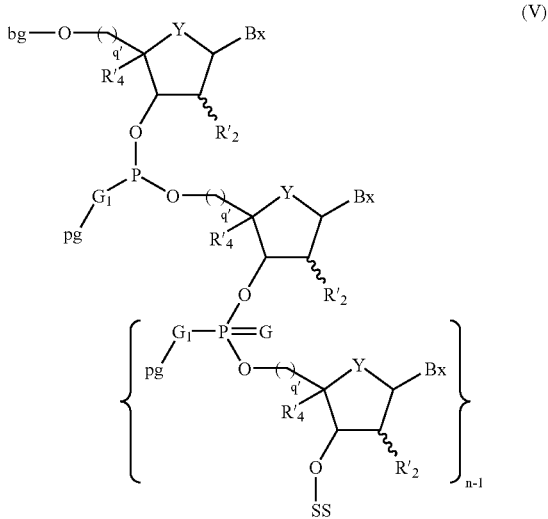
(V)

washing V with a second wash solvent;
oxidizing V to form the support-bound oligonucleotide of formula I; and
washing the support with a third wash solvent;
wherein, at least one of the first, second and third wash solvents comprises a solvent other than acetonitrile.

In other embodiments, the present invention provides a process of synthesizing an oligonucleotide of formula X, said process comprising:

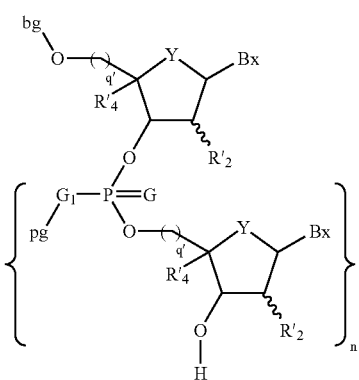

(X)

wherein Y is O, S, $CH_2$, CHF, $CF_2$ or —CH=CH—,
bg is a 5'-blocking group;
n is a positive integer;
each $R'_2$ is, independently, H, OH, protected OH, a 2'-substituent, or together with $R'_4$ forms a bridge;
each $R'_4$ is, independently, H or together with $R'_2$ forms a bridge;
each Bx is independently a nucleobase;
each pg is independently a phosphorus protecting group;
each G is O or S; each $G_1$ is O or S;
each q' is independently 0 or 1; and
SS is a solid support; said process comprising:
on a solid support, contacting a support-bound synthon IIa:

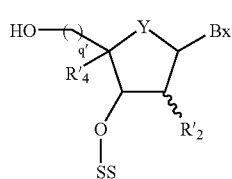

IIa with a deblocking agent to produce a deprotected synthon IIIa:

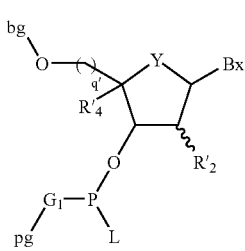

IIIa washing IIIa with a first wash solvent;
contacting IIIa with a nucleoside amidite of formula IV:

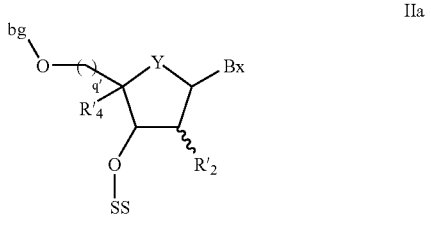

(IV)

to form a phosphitylated intermediate of formula Va:

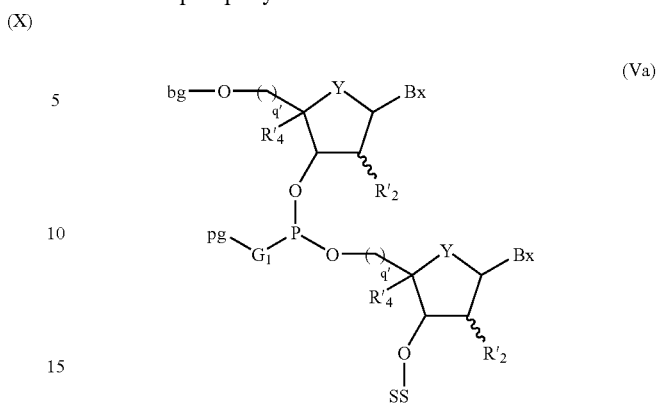

(Va)

washing Va with a second wash solvent;
capping unreacted IIa with a capping reagent;
washing Va with a third wash solvent;
oxidizing the phosphitylated intermediate of formula Va to form support-bound oligonucleotide of formula VI:

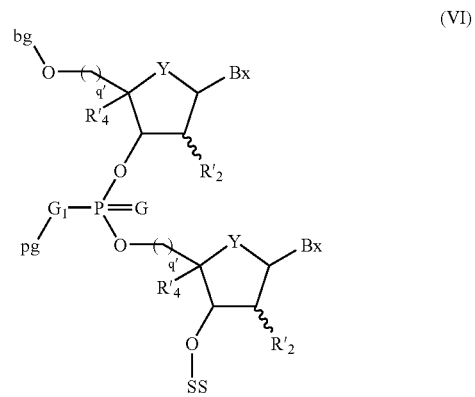

(VI)

washing VI with a fourth wash solvent;
repeating each of the above steps for n–1 cycles, where n is a positive integer, to form a phosphorus-protected support-bound oligonucleotide of formula I:

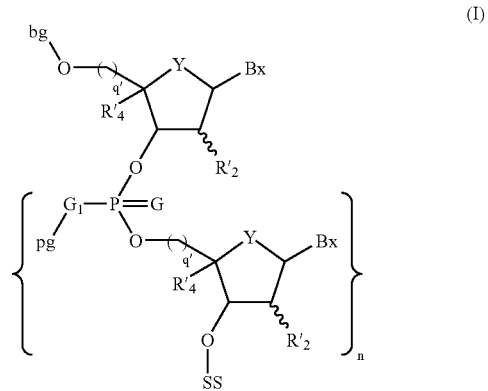

(I)

removing the protecting groups pg from I to form a support-bound compound of formula VII:

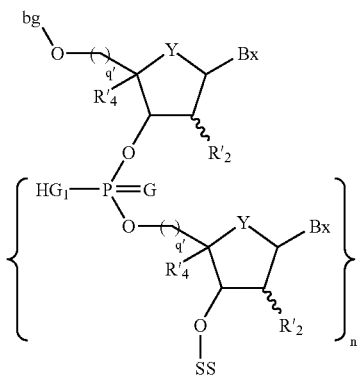

(VII)

washing VII with a sixth wash solvent; and cleaving VII from the support, to produce the oligonucleotide of formula X;

wherein, at least one of the first, second, third, fourth, fifth and sixth solvents comprises a solvent other than acetonitrile.

In some embodiments, the present invention provides a method of synthesizing a phosphorus-protected oligonucleotide having the formula I on a solid support:

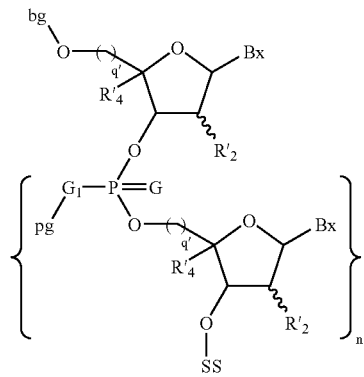

(I)

wherein bg is a 5'-blocking group;

n is a positive integer;

each $R'_2$ is, independently, H, OH, OZ (wherein Z is a removable protecting group), a 2'-substituent, or together with $R'_4$ forms a bridge;

each $R'_4$ is, independently, H or together with $R'_2$ forms a bridge;

each Bx is independently a nucleobase;
each pg is independently a phosphorus protecting group;
each of $G_1$ and G is, independently, O or S;

each q' is independently 0 or 1; and

SS is a solid support; said process comprising:

contacting a support-bound synthon II:

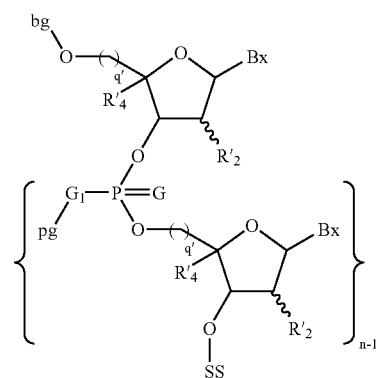

(II)

with a deblocking agent to produce a deblocked synthon III:

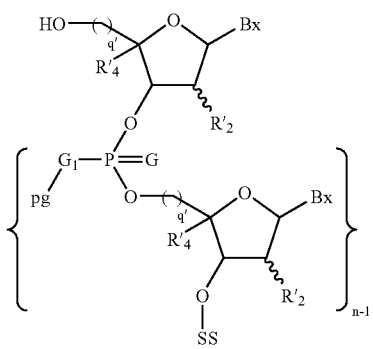

(III)

contacting III with a first wash solvent;

contacting III with a phosphoramidite of formula IV:

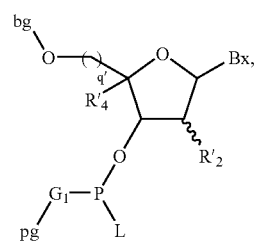

(IV)

wherein L is an amine leaving group, to form a phosphitylated intermediate of formula V:

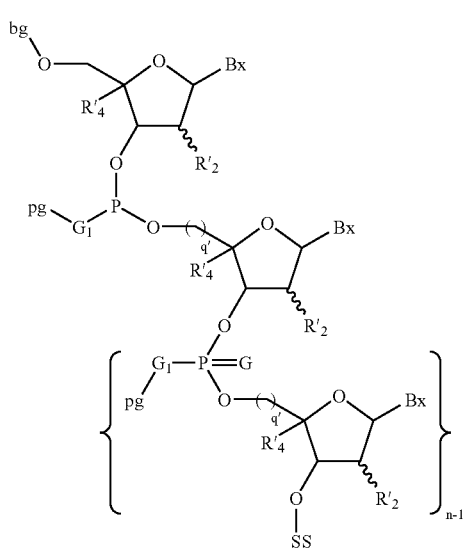

(V)

washing V with a second wash solvent;
capping unreacted III with a capping reagent;
washing V with a third wash solvent;
oxidizing the phosphitylated intermediate of formula V to form the support-bound oligonucleotide of formula I; and
washing I with a fourth wash solvent,
wherein, at least one of the first, second, third and fourth wash solvents comprises a solvent other than acetonitrile.

In other embodiments, the present invention provides a process of synthesizing an oligonucleotide of formula X, said process comprising:

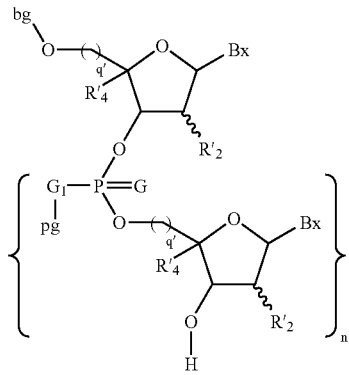

(X)

wherein bg is a 5'-blocking group;
n is a positive integer;
each $R'_2$ is, independently, H, OH, protected OH, a 2'-substituent, or together with $R'_4$ forms a bridge;
each $R'_4$ is, independently, H or together with $R'_2$ forms a bridge;
each Bx is independently a nucleobase;
each pg is independently a phosphorus protecting group;
each G is O or S; each $G_1$ is O or S;
each q' is independently 0 or 1; and SS is a solid support; said process comprising:
on a solid support, contacting a support-bound synthon IIa:

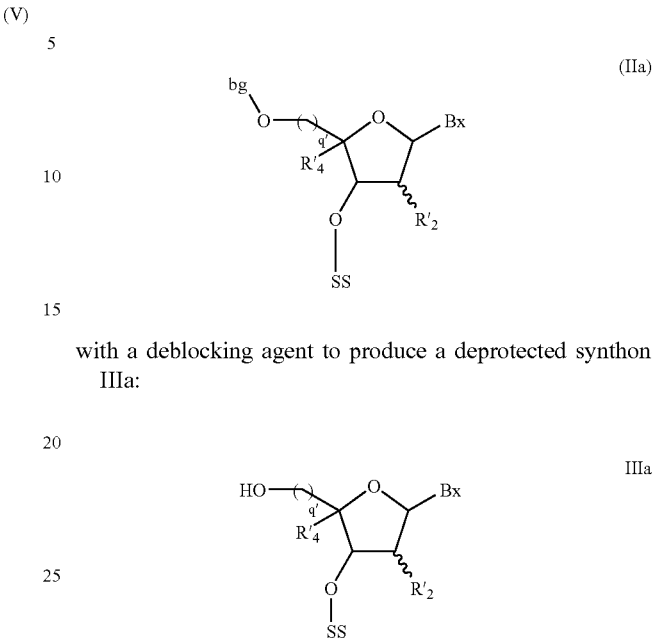

(IIa)

with a deblocking agent to produce a deprotected synthon IIIa:

(IIIa)

washing IIIa with a first wash solvent;
contacting IIa with a nucleoside amidite of formula IV:

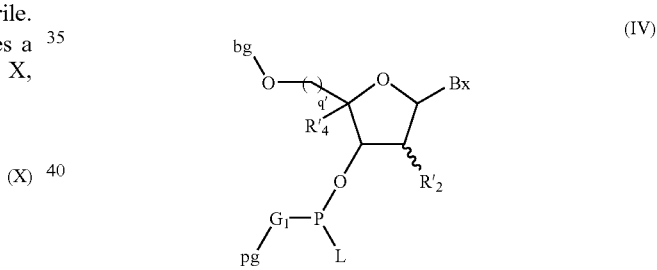

(IV)

to form a phosphitylated intermediate of formula Va:

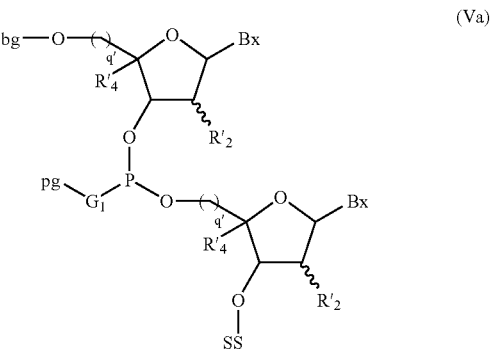

(Va)

washing Va with a second wash solvent;
capping unreacted IIIa with a capping reagent;
washing Va with a third wash solvent;

oxidizing the phosphitylated intermediate of formula Va to form support-bound oligonucleotide of formula VI:

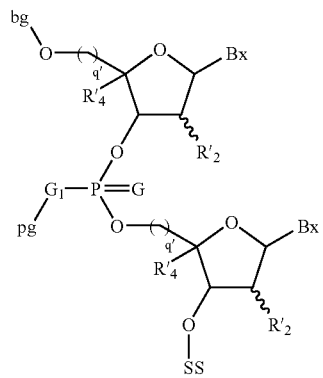
(VI)

washing VI with a fourth wash solvent;
repeating each of the above steps for n–1 cycles, where n is a positive integer, to form a phosphorus-protected support-bound oligonucleotide of formula I:

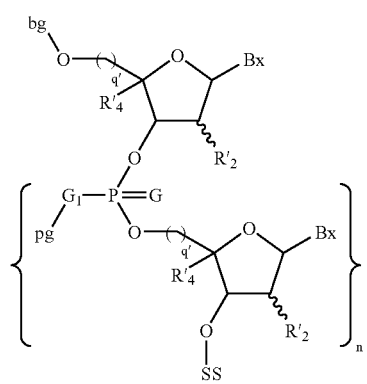
(I)

removing the protecting groups pg from I to form a support-bound compound of formula VII:

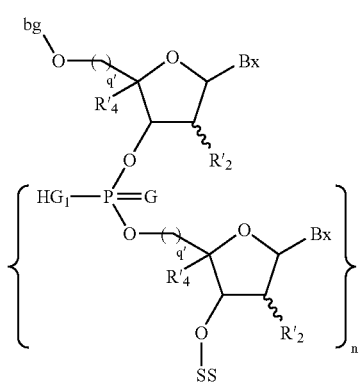
(VII)

washing VII with a sixth wash solvent; and
cleaving VII from the support, to produce the oligonucleotide of formula X;

wherein, at least one of the first, second, third, fourth, fifth and sixth solvents comprises a solvent other than acetonitrile.

In some embodiments, the present invention provides a process of synthesizing an oligonucleotide of formula XI, said process comprising:

process of synthesizing an oligonucleotide of formula XI, said process comprising:

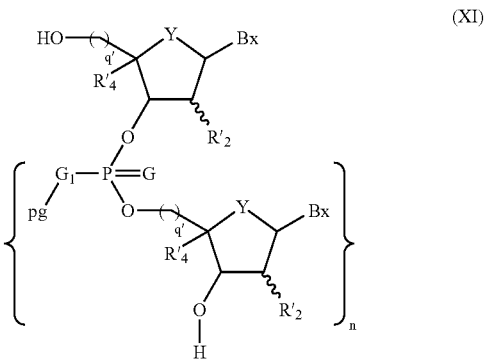
(XI)

wherein n is a positive integer;
each $R'_2$ is, independently, H, OH, protected OH, a 2'-substituent, or together with $R'_4$ forms a bridge;
each $R'_4$ is, independently, H or together with $R'_2$ forms a bridge;
each Bx is independently a nucleobase;
each pg is independently a phosphorus protecting group;
each G is O or S; $G_1$ is O or S
each q' is independently 0 or 1; and
SS is a solid support; said process comprising:
on a solid support, contacting a support-bound synthon IIa:

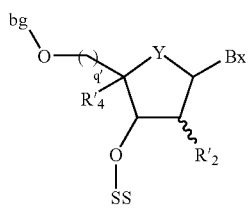
IIa with a deblocking agent to produce a deprotected synthon IIIa:

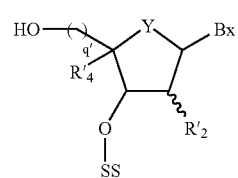
IIIa washing IIIa with a first wash solvent;

contacting IIIa with a nucleoside amidite of formula IV:

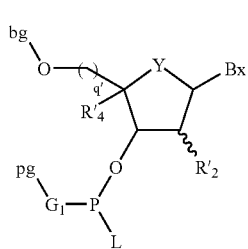
(IV)

to form a phosphitylated intermediate of formula Va:

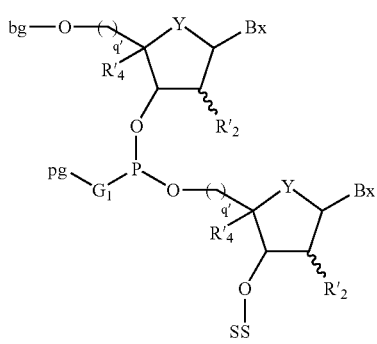
(Va)

washing Va with a second wash solvent;
capping unreacted IIIa with a capping reagent;
washing Va with a third wash solvent;
oxidizing the phosphitylated intermediate of formula Va to form support-bound oligonucleotide of formula VI:

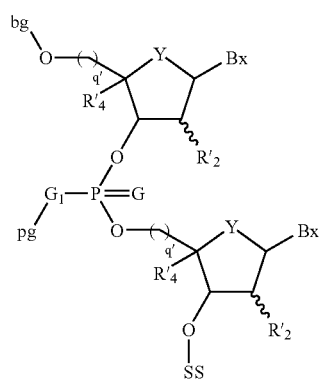
(VI)

washing VI with a fourth wash solvent;
repeating steps (a)-(f) for n−1 cycles, where n is a positive integer, to formn a phosphorus-protected support-bound oligonucleotide of formula I:

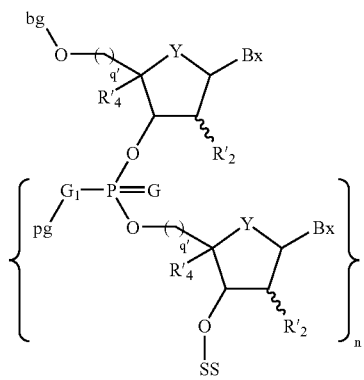
(I)

removing the protecting groups pg from I to form a support-bound compound of formula VII:

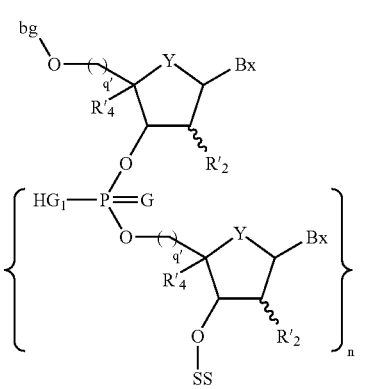
(VII)

washing VII with a sixth wash solvent; and
cleaving VII from the support, to produce the oligonucleotide of formula X:

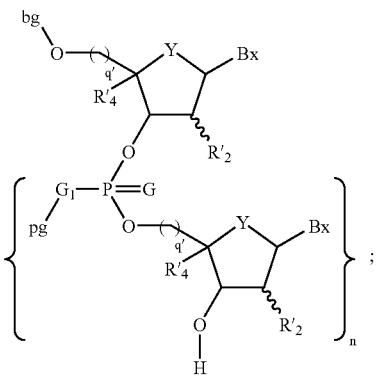
(X)

wherein, at least one of the first, second, third, fourth, fifth and sixth solvents comprises a solvent other than acetonitrile.

In other embodiments, the present invention provides a process of synthesizing an oligonucleotide of formula XI, said process comprising:

to form a phosphitylated intermediate of formula Va:

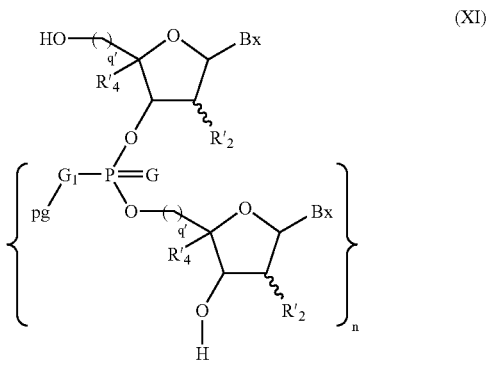
(XI)

wherein n is a positive integer;
each R'$_2$ is, independently, H, OH, OZ (wherein Z is a removable protecting group), a 2'-substituent, or together with R'$_4$ forms a bridge;
each R'$_4$ is, independently, H or together with R'$_2$ forms a bridge;
each Bx is independently a nucleobase;
each pg is independently a phosphorus protecting group;
each G is O or S; G$_1$ is O or S;
each q' is independently 0 or 1; and
SS is a solid support; said process comprising:
on a solid support, contacting a support-bound synthon IIa:

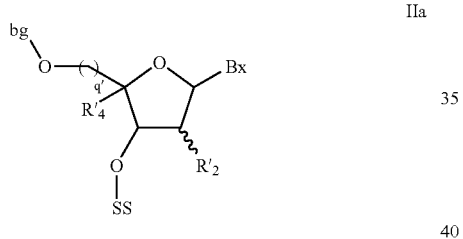
IIa with a deblocking agent to produce a deprotected synthon IIIa:

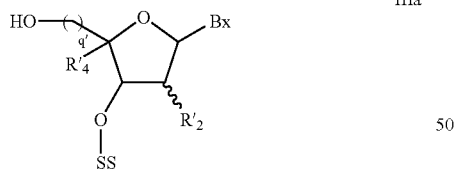
IIIa washing IIIa with a first wash solvent;
contacting IIIa with a nucleoside amidite of formula IV:

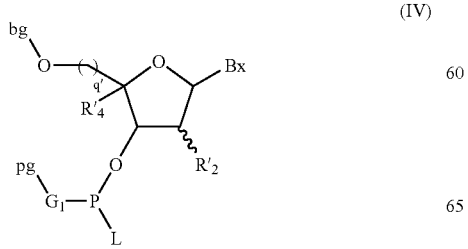
(IV)

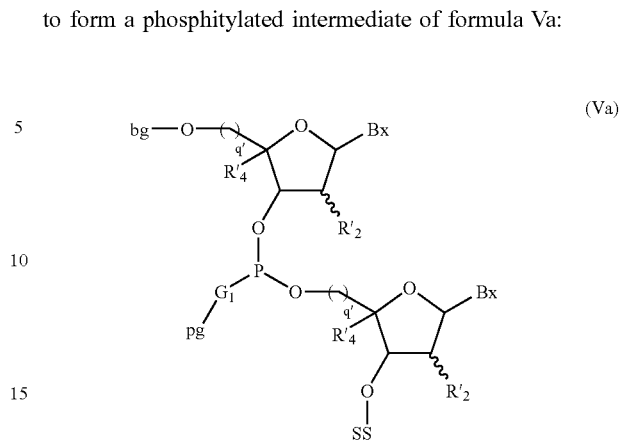
(Va)

washing Va with a second wash solvent;
capping unreacted IIa with a capping reagent;
washing Va with a third wash solvent;
oxidizing the phosphitylated intermediate of formula Va to form support-bound oligonucleotide of formula VI:

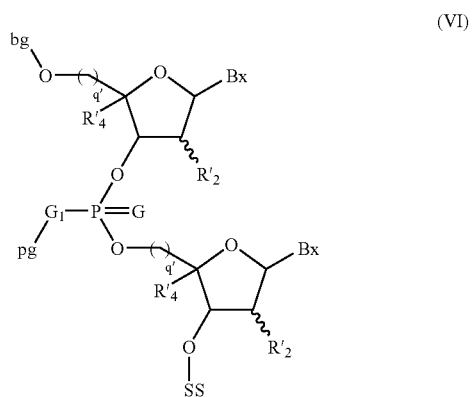
(VI)

washing I with a fourth wash solvent;
repeating steps (a)-(f) for n-1 cycles, where n is a positive integer, to form a phosphorus-protected support-bound oligonucleotide of formula I:

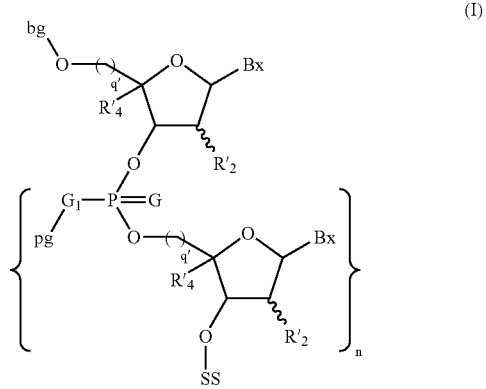
(I)

removing the protecting groups pg from I to form a support-bound compound of formula VII:

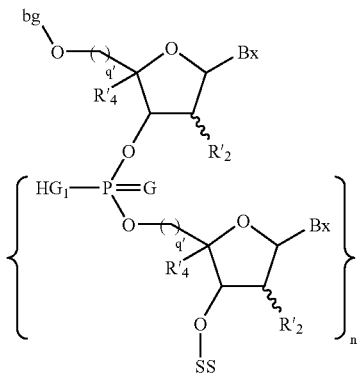

(VII)

washing VII with a sixth wash solvent; and
cleaving VII from the support, to produce the oligonucleotide of formula X:

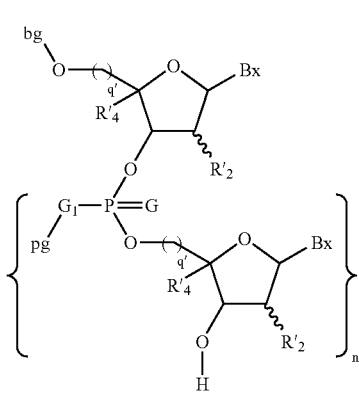

(X)

wherein, at least one of the first, second, third, fourth, fifth and sixth solvents comprises a solvent other than acetonitrile.

The present inventors have found that oligomeric compounds, such as oligonucleotides, may be synthesized on a solid support using solvents other than acetonitrile as solvent wash between additions of reagent to the solid phase synthesis column. The use of alternative solvents surprisingly results in high-quality oligomeric compounds, at high yields, while offering considerable savings in solvent costs. In particular, the inventors have discovered that one or more solvent wash employed to push reagents onto the column, to wash the column after reaction, or both, may comprise a solvent other than acetonitrile, and in preferred embodiments, may consist essentially of a solvent other than acetonitrile.

In regard to the present invention, the term "solid support" shall have the meaning customary in the art. In particular, solid supports include controlled pore glass or a polymeric support, such as a bead, including a polyvinyl acetate or a polystyrene bead.

The term "column" refers to a container that holds a quantity of solid support during solid phase synthesis. While the term commonly refers to fixed bed reactors, it can also refer to stirred bed reactors as well. The column may be made of a commonly used material.

The term "column volume" shall mean the total interior volume of a column.

Unless otherwise stated herein, use of the singular shall not exclude the plural. For example, "an alkane" shall include "one or more alkane or mixtures thereof," such as hexane, heptane, octane, and mixtures thereof; "a heteroaromatic solvent" shall include a single heteroaromatic solvent, as well as mixtures of plural heteroaromatic solvents, for example: pyridine, lutidine, a mixture of pyridine and lutidine, etc.

In some embodiments of the invention, a solvent other than acetonitrile is used after deblocking the 5'-position of a support-bound synthon (e.g. detritylation), after capping of unreacted support-bound synthons, and/or after oxidation of phosphorus from a P(III) to a P(V) oxidation state (e.g. thiation with phenyl acetyl disulfide (PADS)). In particular embodiments, a solvent other than acetonitrile is used after deblocking, capping and oxidation steps. In other embodiments, a solvent other than acetonitrile is used after deblocking and capping steps. In other embodiments, a solvent other than acetonitrile is used after the oxidation step only.

The term "solvent wash" as used herein means a solvent employed in solid phase synthesis of oligomeric compounds to push reagents onto a solid phase synthesis column, to wash unreacted reagent and solution-phase side-products from the column, or both. A solvent wash other than acetonitrile, as used herein, includes alkylated benzenes (e.g. toluene, ethylbenzene, n-propylbenzene, i-propylbenzene, o-xylene, m-xylene, p-xylene, etc.), haloalkyl benzenes (e.g. trifluoromethylbenzene, trichloromethylbenzene, etc.), alcohols (e.g. propanol), alkanes (e.g. hexane, heptane, etc.), halogenated benzenes (fluorobenzene, chlorobenzene, bromobenzene), an alkyl alkylate (such as ethylacetate, propylacetate, etc.), an aryl amine (such as pyridine, lutidine, etc.). In preferred embodiments, the solvent wash other than acetonitrile comprises toluene or pyridine. In particularly preferred embodiments, the solvent wash other than acetonitrile consists essentially of toluene or pyridine.

The phrase, "consists essentially of" and grammatical variants thereof, indicates that the solvent wash, before being applied to the column, is essentially free of any other solvents, except for those which are inevitably dissolved in reagent grade solvents as received from a commercial supplier. In this context it is noted that mixtures of solvents may be employed, in some embodiments, where part of the normally employed volume of acetonitrile is replaced with a solvent other than acetonitrile. In some embodiments, at least half the ordinarily used aliquot of acetonitrile is replaced with a solvent other than acetonitrile. In other embodiments, at least three quarters of the ordinary aliquot of acetonitrile is replaced with a solvent other than acetonitrile. In still other embodiments, at least about 90 percent of the ordinary aliquot of acetonitrile is replaced with a solvent other than acetonitrile. In other embodiments, the ordinary aliquot of acetonitrile is entirely replaced with a solvent other than acetonitrile that is substantially free of acetonitrile.

The person skilled in the art will note that "solvent other than acetonitrile" and variants thereof mean that the solvent, prior to being applied to the column, comprises at least one solvent other than acetonitrile. The person skilled in the art will further appreciate that once a solvent wash has been applied to a column, it will become contaminated to a degree with whatever solvent, reagent, side-products, activator(s), catalyst(s), etc. that may be on the column at the time. As the solvents that may be on a column before the solvent wash is applied thereto will typically include acetonitrile, the person skilled in the art will recognize that the frame of reference for determining whether a solvent other than acetonitrile consists essentially of a solvent other than acetonitrile is prior to its being applied to the column.

The general procedure for synthesizing an oligonucleotide is described in detail above. The present invention involves replacing one or more acetonitrile washes with a wash using a solvent other than acetonitrile.

The present invention is concerned with the general problem of decreasing the cost of oligomer synthesis, especially on a large scale. In particular, the present invention provides methods of oligomer synthesis, in which the relatively expensive solvent acetonitrile is replaced with a different solvent during one or more steps of oligonucleotide synthesis, especially during one or more wash steps.

In the context of the present invention, the terms "oligomeric compound" and "oligomer" refer to a polymeric structure capable of hybridizing a region of a nucleic acid molecule, and having at least one phosphate bond between adjacent nucleoside or modified-nucleoside moieties. As discussed below, an oligomer may also comprise additional features, such as one or more stretch of nucleosides, modified nucleoside, or nucleoside mimetics, that are linked to one another by non-phosphate linkages. These additional features may include oligonucleosides, oligonucleotide analogs, modified oligonucleotides and oligonucleotide mimetics. Oligomeric compounds can be single-stranded or double-stranded, and when double-stranded, may include overhangs. An oligomeric compound comprises a backbone of monomeric subunits that share some common structural feature, where each monomeric subunit is linked to an adjacent monomeric subunit by an appropriate linker. Each monomeric subunit is directly or indirectly attached to a heterocyclic base moiety. The linkages joining the monomeric subunits to one another, the monomeric subunits, and the heterocyclic base moieties, can all vary in structure, giving rise to a plurality of motifs for the resulting oligomeric compounds including hemimers, gapmers and chimeras.

One type of monomeric subunit known in the art is a nucleoside, which is a base-sugar combination. The base portion of the nucleoside is normally a heterocyclic base moiety, or nucleobase. The two most common classes of such heterocyclic bases are purines and pyrimidines. A nucleoside having a phosphate group (or a phosphorothioate group) is called a nucleotide. When a plurality of nucleosides are linked by successive phosphate or phosphorothioate groups, the resulting oligomer is called an oligonucleotide.

In the broadest sense, the term "oligonucleotide" refers to an oligomer having a plurality of sugar units linked by phosphate diester (e.g. phospho diester, phosphorothioate diester, phosphorodithioate diester moieties, etc.). In some embodiments of the invention, an oligonucleotide may contain both phospho diester and phosphorothioate diester linkers. In other embodiments, the linkers are all phosphorothioate diester linkers. While phosphodiester linkers are the naturally occurring type of linkers in oligonucleotides, thiophosphate linkers are known to confer favorable characteristics to oligonucleotides in vivo. Hence, it is often preferred to prepare oligonucleotides with at least a portion of the phospho diester moieties replaced by phosphorothioate diester moieties.

A standard oligonucleotide is shown in formula 1 below:

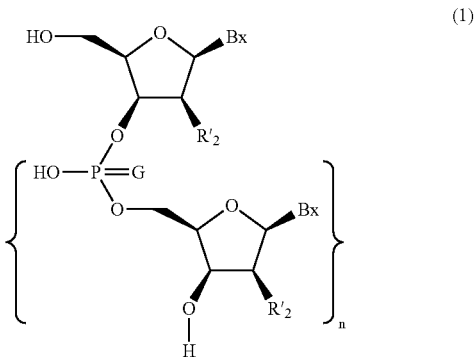

In formula 1, each G is independently O or S, each $R'_2$ is independently H or OH, n is an integer and each Bx is independently a nucleobase as described in greater detail herein. Thus the repeating backbone unit is a ribosyl ring linked to a phosphate or phosphorothioate linker. Selectivity for a particular target sequence is achieved by modification of the sequence of Bx units. This procedure is discussed in greater detail herein.

The 2'-position may be H (i.e. 2'-deoxyribosyl) or OH (ribosyl). It is possible for all $R'_2$ units to be OH, e.g. where the oligomers will be used in siRNA (either single- or double-stranded). It is often desirable for all or part of the oligomer to be 2'-deoxy, e.g. for activation of the RNAse H pathway. In some embodiments of the invention, each of the $R'_2$ groups is H. In other cases, a contiguous stretch sugars are 2'-deoxy, while one or more stretches of the remainder of the oligonucleotide contain ribosyl or 2'-modified ribosyl sugars, as described in more detail herein.

Formula 1 depicts the simplest oligonucleotides, which are also referred to in the art as "first generation" oligonucleotides. Other oligonucleotides are possible, and are encompassed within the meaning of "oligonucleotide" as used herein. In particular, oligonucleotides may contain repeating units where the standard ribosyl unit is replaced with a substituted ribosyl unit (e.g. a 2'-deoxy-2'-substituted ribosyl unit), where the ribosyl unit is replaced by a different sugar entirely (e.g. an arabinosyl or erythrosyl unit), or where the ribosyl unit is replaced by a bridged sugar unit (i.e. a locked nucleic acid). A general formula for an oligonucleotide of this type is depicted in Formula 2.

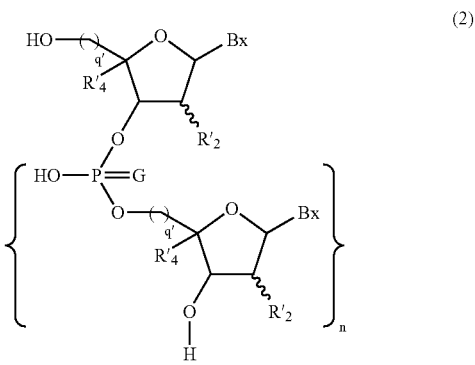

In formula 2, G, Bx and n have the same meanings as in formula 1. The squiggly line joining $R'_2$ to the ring indicates that the 2'-substituent may be in either the down or up configuration. The value of q' may be 0 or 1. $R'_2$ may be H, OH, a protected OH, a 2'-substituent, or may form, together with $R'_4$, a bridge unit. $R'_4$ is either H or, together with $R'_2$, form a bridge.

The person skilled in the art will recognize that when $R'_2$ is in the down configuration and q' is 1, the ring is a ribosyl ring, whereas when $R'_2$ is in the up configuration and q' is 1, the ring is an arabinosyl ring. Likewise, when q' is 0 and $R'_2$ is in the down configuration, the ring is an erythrosyl ring. When $R'_2$ and $R'_4$ are joined to form a bridge, the ring is called a locked nucleic acid (LNA), as described in greater detail herein. In some embodiments, the bridge formed by $R'_2$ and $R'_4$ is $R'_2$—O—$(CH_2)_r$—$R'_4$ (wherein r is 1 or 2) or $R'_2$—$CH_2$—O—$CH_2$—$R'_4$ (the use of $R'_2$ and $R'_4$ in the sub-formulae indicating the points of attachment.) LNA may be present in either α-L- or β-D- conformation. See Vester et al., "LNAzymes: Incorporation of LNA-Type Monomers into DNAzymes Markedly Increases RNA Cleavage," Journal of the American Chemical Society, 2002, 124, 13682-3. Each of these analogs possesses a number of useful characteristics, including resistance to exonuclease activity.

The variable Sug, as used herein, refers to a sugar ring or a modified sugar ring. Sugar rings include ribosyl, 2'-deoxyribosyl, arabinosyl, erythrosyl and other sugar rings. Modified sugar rings include the foregoing sugar rings as modified per the description herein, e.g. at the 2'-position, or by a bridge between the 2'- and 4'-positions as described in further detail herein.

The variable Bx refers to a nucleobase as described further herein. Certain oligonucleotides that utilized arabino-pentofuranosyl nucleotides as building blocks have been described. Damha et. al., J.A.C.S., 1998, 120, 12976-12977; and Damha et. al., Bioconjugate Chem., 1999, 10, 299-305.

Suitable 2'-substituents corresponding to $R'_2$ include: OH, F, O-alkyl (e.g. O-methyl), S-alkyl, N-alkyl, O-alkenyl, S-alkenyl, N-alkenyl; O-alkynyl, S-alkynyl, N-alkynyl; O-alkyl-O-alkyl, wherein the alkyl, alkenyl and alkynyl may be substituted or unsubstituted $C_1$ to $C_{10}$ alkyl or $C_2$ to $C_{10}$ alkenyl or alkynyl, respectively. Particularly preferred are $O[(CH_2)_gO]_hCH_3$, $O(CH_2)_gOCH_3$, $O(CH_2)_gNH_2$, $O(CH_2)_gCH_3$, $O(CH_2)_gONH_2$, and $O(CH_2)_gON[(CH_2)_gCH_3]_2$, where g and h are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred 2'-modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504). A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylamino-ethoxyethoxy (also known in the art as 2'-O-dimethyl-amino-ethoxy-ethyl or 2'-DMAEOE), i.e., 2'-O—$CH_2$—O—$CH_2$—$N(CH_3)_2$, also described in examples hereinbelow.

Other preferred modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide.

Further representative substituent groups include groups of formula $I_a$ or $II_a$:

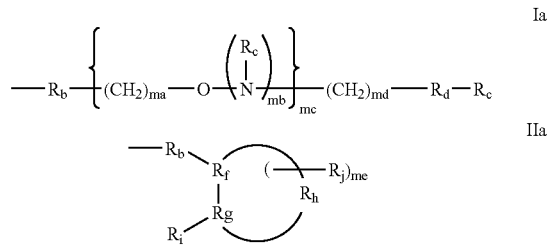

wherein:
$R_b$ is O, S or NH;
$R_d$ is a single bond, O or C(=O);
$R_e$ is $C_1$-$C_{10}$ alkyl, $N(R_k)(R_m)$, $N(R_k)(R_n)$, N=$C(R_p)(R_q)$, N=$C(R_p)$( has formula $III_a$;

each $R_s$, $R_t$, $R_u$ and $R_v$ is, independently, hydrogen, $C(O)R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_u$ and $R_v$, together form a phthalimido moiety with the nitrogen atom to which they are attached;

each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_k$ is hydrogen, a nitrogen protecting group or —$R_x$-$R_y$;
$R_p$ is hydrogen, a nitrogen protecting group or —$R_x$-$R_y$;
$R_x$ is a bond or a linking moiety;
$R_y$ is a chemical functional group, a conjugate group or a solid support medium;

each $R_m$ and $R_n$ is, independently, H, a nitrogen protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester;

or $R_m$ and $R_n$, together, are a nitrogen protecting group, are joined in a ring structure that optionally includes an additional heteroatom selected from N and O or are a chemical functional group;

$R_i$ is $OR_z$, $SR_z$, or $N(R_z)_2$;

each $R_z$ is, independently, H, $C_1$-$C_8$ alkyl, $C_1$-$C_8$ haloalkyl, C(=NH)N(H)$R_u$, C(=O)N(H)$R_u$ or OC(=O)N(H)$R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)$ $OR_k$, halo, $SR_k$ or CN;

$m_a$ is 1 to about 10;

each mb is, independently, 0 or 1;

mc is 0 or an integer from 1 to 10;

md is an integer from 1 to 10;

me is from 0, 1 or 2; and provided that when mc is 0, md is greater than 1.

Representative substituents groups of Formula I are disclosed in U.S. patent application Ser. No. 09/130,973, filed Aug. 7, 1998, entitled "Capped 2'-Oxyethoxy Oligonucleotides," hereby incorporated by reference in its entirety. Representative cyclic substituent groups of Formula II are disclosed in U.S. patent application Ser. No. 09/123,108, filed Jul. 27, 1998, entitled "RNA Targeted 2'-Modified Oligonucleotides that are Conformationally Preorganized," hereby incorporated by reference in its entirety.

Particularly preferred sugar substituent groups include $O[(CH_2)_gO]_hCH_3$, $O(CH_2)_gOCH_3$, $O(CH_2)_gNH_2$, $O(CH_2)_gCH_3$, $O(CH_2)_gONH_2$, and $O(CH_2)_gON[(CH_2)_gCH_3]_2$, where g and h are from 1 to about 10.

Some preferred oligomeric compounds of the invention contain at least one nucleoside having one of the following substituent groups: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligomeric compound, or a group for improving the pharmacodynamic properties of an oligomeric compound, and other substituents having similar properties. A preferred modification includes 2'-methoxyethoxy [2'-O—$CH_2CH_2OCH_3$, also known as 2'-O-(2-methoxyethyl) or 2'-MOE] (Martin et al., Helv. Chim. Acta, 1995, 78, 486), i.e., an alkoxyalkoxy group. A further preferred modification is 2'-dimethylaminooxyethoxy, i.e., a $O(CH_2)_2ON(CH_3)_2$ group, also known as 2'-DMAOE. Representative aminooxy substituent groups are described in co-owned U.S. patent application Ser. No. 09/344,260, filed Jun. 25, 1999, entitled "Aminooxy-Functionalized Oligomers"; and U.S. patent application Ser. No. 09/370,541, filed Aug. 9, 1999, entitled "Aminooxy-Functionalized Oligomers and Methods for Making Same;" hereby incorporated by reference in their entirety.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on nucleosides and oligomers, particularly the 3' position of the sugar on the 3' terminal nucleoside or at a 3'-position of a nucleoside that has a linkage from the 2'-position such as a 2'-5' linked oligomer and at the 5' position of a 5' terminal nucleoside. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

Representative guanidino substituent groups that are shown in formula III and IV are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. Pat. No. 6,147,200 which is hereby incorporated by reference in its entirety. Representative dimethylaminoethyloxyethyl substituent groups are disclosed in International Patent Application PCT/US99/17895, entitled "2'-O-Dimethylaminoethyloxyethyl-Modified Oligonucleotides", filed Aug. 6, 1999, hereby incorporated by reference in its entirety. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally preferred. Within the oligonucleotide structure, the phosphate groups are commonly referred to as forming the internucleoside linkages of the oligonucleotide. The normal internucleoside linkage of RNA and DNA is a 3' to 5' phosphodiester linkage.

While the present invention may be adapted to produce oligonucleotides for any desired end use (e.g. as probes for us in the polymerase chain reaction), one preferred use of the oligonucleotides is in antisense therapeutics. One mode of action that is often employed in antisense therapeutics is the so-called RNAse H mechanism, whereby a strand of DNA is introduced into a cell, where the DNA hybridizes to a strand of RNA. The DNA-RNA hybrid is recognized by an endonuclease, RNAse H, which cleaves the RNA strand. In normal cases, the RNA strand is messenger RNA (mRNA), which, after it has been cleaved, cannot be translated into the corresponding peptide or protein sequence in the ribosomes. In this way, DNA may be employed as an agent for modulating the expression of certain genes.

It has been found that by incorporating short stretches of DNA into an oligonucleotide, the RNAse H mechanism can be effectively used to modulate expression of target peptides or proteins. In some embodiments of the invention, an oligonucleotide incorporating a stretch of DNA and a stretch of RNA or 2'-modified RNA can be used to effectively modulate gene expression. In preferred embodiments, the oligonucleotide comprises a stretch of DNA flanked by two stretches of 2'-modified RNA. Preferred 2'-modifications include 2'-MOE as described herein.

The ribosyl sugar moiety has also been extensively studied to evaluate the effect its modification has on the properties of oligonucleotides relative to unmodified oligonucleotides. The 2'-position of the sugar moiety is one of the most studied sites for modification. Certain 2'-substituent groups have been shown to increase the lipohpilicity and enhance properties such as binding affinity to target RNA, chemical stability and nuclease resistance of oligonucleotides. Many of the modifications at the 2'-position that show enhanced binding affinity also force the sugar ring into the $C_3$-endo conformation.

RNA exists in what has been termed "A Form" geometry while DNA exists in "B Form" geometry. In general, RNA:RNA duplexes are more stable, or have higher melting temperatures (Tm) than DNA:DNA duplexes (Sanger et al., *Principles of Nucleic Acid Structure*, 1984, Springer-Verlag; New York, N.Y.; Lesnik et al., *Biochemistry*, 1995, 34, 10807-10815; Conte et al., *Nucleic Acids Res.*, 1997, 25, 2627-2634). The increased stability of RNA has been attributed to several structural features, most notably the improved base stacking interactions that result from an A-form geometry (Searle et al., *Nucleic Acids Res.*, 1993, 21, 2051-2056). The presence of the 2' hydroxyl in RNA biases the sugar toward a C3' endo pucker, i.e., also designated as Northern pucker, which causes the duplex to favor the A-form geometry. On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.). In addition, the 2' hydroxyl groups of RNA can form a network of water mediated hydrogen bonds that help stabilize the RNA duplex (Egli et al., *Biochemistry*, 1996, 35, 8489-8494).

DNA:RNA hybrid duplexes, however, are usually less stable than pure RNA:RNA duplexes, and depending on their sequence may be either more or less stable than DNA:DNA duplexes (Searle et al., *Nucleic Acids Res.*, 1993, 21, 2051-2056). The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., *Biochemistry*, 1995, 34, 4969-4982; Horton et al., *J. Mol. Biol.*, 1996, 264, 521-533). The stability of a DNA:RNA hybrid is central to antisense therapies as the mechanism requires the binding of a modified DNA strand to a mRNA strand. To effectively inhibit the mRNA, the antisense DNA should have a very high binding affinity with the mRNA. Otherwise, the desired interaction between the DNA and target mRNA strand will occur infrequently, thereby decreasing the efficacy of the antisense oligonucleotide.

Various synthetic modifications have been proposed to increase nuclease resistance, or to enhance the affinity of the antisense strand for its target mRNA (Crooke et al., *Med. Res. Rev.*, 1996, 16, 319-344; De Mesmaeker et al., *Acc. Chem. Res.*, 1995, 28, 366-374). A variety of modified phosphorus-containing linkages have been studied as replacements for the natural, readily cleaved phosphodiester linkage in oligonucleotides. In general, most of them, such as the phosphorothioate, phosphoramidates, phosphonates and phosphorodithioates all result in oligonucleotides with reduced binding to complementary targets and decreased hybrid stability.

RNA exists in what has been termed "A Form" geometry while DNA exists in "B Form" geometry. In general, RNA:RNA duplexes are more stable, or have higher melting temperatures (Tm) than DNA:DNA duplexes (Sanger et al., *Principles of Nucleic Acid Structure*, 1984, Springer-Verlag; New York, N.Y.; Lesnik et al., *Biochemistry*, 1995, 34, 10807-10815; Conte et al., *Nucleic Acids Res.*, 1997, 25, 2627-2634). The increased stability of RNA has been attributed to several structural features, most notably the improved base stacking interactions that result from an A-form geometry (Searle et al., *Nucleic Acids Res.*, 1993, 21, 2051-2056). The presence of the 2=hydroxyl in RNA biases the sugar toward a C3=endo pucker, i.e., also designated as Northern pucker, which causes the duplex to favor the A-form geometry. On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.). In addition, the 2=hydroxyl groups of RNA can form a network of water mediated hydrogen bonds that help stabilize the RNA duplex (Egli et al., *Biochemistry*, 1996, 35, 8489-8494).

DNA:RNA hybrid duplexes, however, are usually less stable than pure RNA:RNA duplexes and, depending on their sequence, may be either more or less stable than DNA:DNA duplexes (Searle et al., *Nucleic Acids Res.*, 1993, 21, 2051-2056). The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., *Biochemistry*, 1995, 34, 4969-4982; Horton et al., *J. Mol. Biol.*, 1996, 264, 521-533). The stability of a DNA:RNA hybrid a significant aspect of antisense therapies, as the proposed mechanism requires the binding of a modified DNA strand to a mRNA strand. Ideally, the antisense DNA should have a very high binding affinity with the mRNA. Otherwise, the desired interaction between the DNA and target mRNA strand will occur infrequently, thereby decreasing the efficacy of the antisense oligonucleotide.

One synthetic 2'-modification that imparts increased nuclease resistance and a very high binding affinity to nucleotides is the 2=-methoxyethoxy (MOE, 2'-OCH$_2$CH$_2$OCH$_3$) side chain (Baker et al., *J. Biol. Chem.*, 1997, 272, 11944-12000; Freier et al., *Nucleic Acids Res.*, 1997, 25, 4429-4443). One of the immediate advantages of the MOE substitution is the improvement in binding affinity, which is greater than many similar 2' modifications such as O-methyl, O-propyl, and O-aminopropyl (Freier and Altmann, *Nucleic Acids Research*, (1997) 25:4429-4443). 2=-O-Methoxyethyl-substituted oligonucleotides also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926). Relative to DNA, they display improved RNA affinity and higher nuclease resistance. Chimeric oligonucleotides with 2=-O-methoxyethyl-ribonucleoside wings and a central DNA-phosphorothioate window also have been shown to effectively reduce the growth of tumors in animal models at low doses. MOE substituted oligonucleotides have shown outstanding promise as antisense agents in several disease states. One such MOE substituted oligonucleotide is presently being investigated in clinical trials for the treatment of CMV retinitis.

LNAs (oligonucleotides wherein the 2' and 4' positions are connected by a bridge) also form duplexes with complementary DNA, RNA or LNA with high thermal affinities.

Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

LNAs in which the 2'-hydroxyl group is linked to the 4' carbon atom of the sugar ring thereby forming a 2'-C,4'-C-oxymethylene linkage thereby forming a bicyclic sugar moiety. The linkage is preferably a methelyne ($-CH_2-$)$_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. Other preferred bridge groups include the 2'-$CH_2OCH_2$-4' bridge.

While the present invention is concerned primarily with oligonucleotides, some oligonucleotide mimetics may, with appropriate changes to the starting materials, also be prepared by processes according to the present invention. Oligonucleotide mimetics include compounds in which the oligonucleotide sugar has been replaced with a heterocyclic or carbocyclic ring structure. Such compounds are depicted in Formula 3, below.

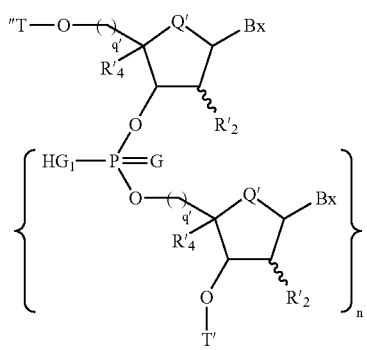

(3)

In Formula 3, G, $G_1$, Bx, n, $R'_2$ and $R'_4$ each have the meanings previously defined. The groups T' and T" are each H, or conjugate groups, such as protecting groups and substituents. Each Q' is independently O, S, NR''', C(R''')$_2$, or —CR'''=CR'''—, where each R''' is H, alkyl, or where two R''' groups are on the same or adjacent carbon atoms, they may form a carbocyclic or heterocyclic ring, wherein the ring contains one or two of N, O or S. Preferred values of R''' are H and $C_1$-$C_4$ alkyl.

The foregoing oligonucleotides and oligonucleotide mimetics may be manufactured by any art-recognized method of forming phosphate diester or phosphorothioate diester linkages between successive nucleoside or nucleoside mimetic units. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

A preferred process of synthesizing oligomeric compounds utilizes phosphoramidite chemistry on a support media. The phosphoramidites can modified at the heterocyclic base, the sugar, or both positions to enable the synthesis of oligonucleotides and modified oligonucleotides.

Illustrative examples of the synthesis of particular modified oligonucleotides may be found in the following U.S. patents or pending patent applications, each of which is commonly assigned with this application: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No.5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides oligonucleotides having 3-deazapurines; U.S. Pat. Nos. 5,223,168, issued Jun. 29, 1993, and 5,608,046, both drawn to conjugated 4'-desmethyl nucleoside analogs; U.S. Pat. Nos. 5,602,240, and 5,610,289, drawn to backbone modified oligonucleotide analogs; and U.S. patent application Ser. No. 08/383,666, filed Feb. 3, 1995, and U.S. Pat. No. 5,459,255, drawn to, inter alia, methods of synthesizing 2'-fluoro-oligonucleotides.

The phosphoramidite method is as follows:

Phosphoramidites are prepared by reacting a suitable nucleoside or modified nucleoside (formula 4) with a phosphorodiamidite (formula 5) to form a phosphoramidite (formula 6).

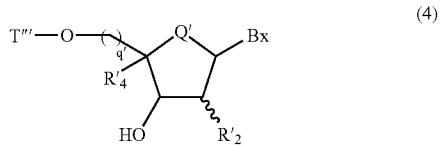

(4)

(5)

(6)

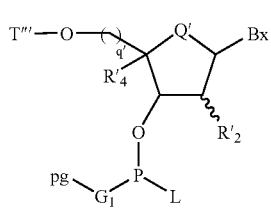

Each of the variables Q', Bx, R'$_2$, R'$_4$, and q' is as previously defined. L is an amine leaving group; pg is a phosphorus protecting group; G$_1$ is O or S; and T''' is a hydroxyl protecting group, each as more specifically defined herein.

A support-bound nucleoside of Formula 7 is first deprotected at the 5'-position (resulting in a free 5'-OH group), after which a first amidite is coupled to a support-bound nucleoside to form a support-bound dimer of Formula 8, which is then oxidized, and subjected to a capping step to form a support bound dimer of Formula 9.

(7)

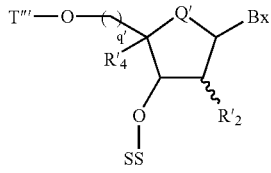

(8)

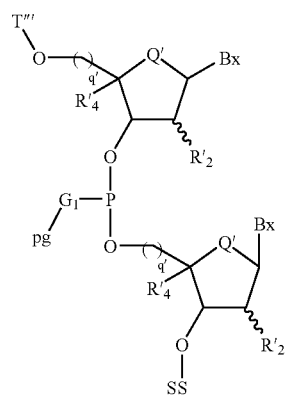

(9)

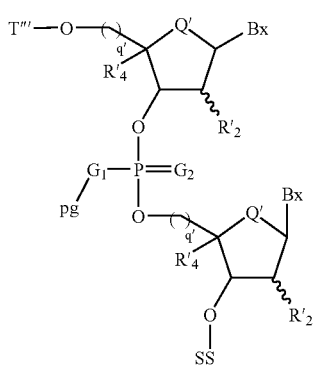

The 5'-deprotection, coupling, oxidation and capping steps are then repeated n–2 times to form a support-bound oligomer of Formula 10.

(10)

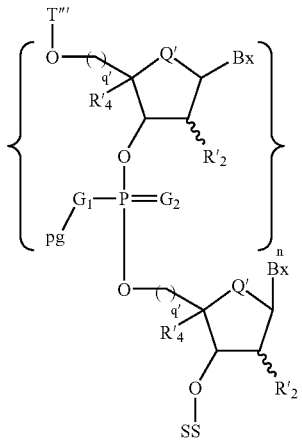

This compound is then cleaved from the solid support, 5'-deprotected, and purified to yield an oligomer of Formula 3, as described herein.

In each of the foregoing Formulae, SS represents a solid support, each pg is a phosphorus protecting group as defined herein, n is an integer, G$_1$ and G$_2$ are independently O or S, and each Bx, R'$_2$, R'$_4$, Q', and q' is independently as defined in Formula 3.

In addition to phosphate diester and phosphorothioate diester linkages, other linkers are known in the art. While the primary concern of the present invention has to do with phosphate diester and phosphorothioate diester oligonucleotides, chimeric compounds having more than one type of linkage, as well as oligomers having non-phosphate/phosphorothioate diester linkages as described in further detail below, are also contemplated in whole or in part within the context of the present invention.

Exemplary non-phosphate/phosphorothioate diester linkages contemplated within the skill of the art include: phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates. Additional linkages include: thiodiester (—O—C(O)—S—), thionocarbamate (—O—C(O) (NJ)—S—), siloxane (—O—Si(J)$_2$—O—), carbamate (—O—C(O)—NH— and —NH—C(O)—O—), sulfamate (—O—S(O)(O)—N— and —N—S(O)(O)—N—, morpholino sulfamide (—O—S(O)(N(morpholino)-), sulfonamide (—O—SO$_2$—NH—), sulfide (—CH$_2$—S—CH$_2$—), sulfonate (—O—SO$_2$—CH$_2$—), N,N'-dimethylhydrazine (—CH$_2$—N(CH$_3$)—N(CH$_3$)—), thioformacetal (—S—CH$_2$—O—), formacetal (—O—CH$_2$—O—), thioketal (—S—C(J)$_2$-O—), ketal (—O—C(J)$_2$-O—), amine (—NH—CH$_2$—CH$_2$—), hydroxylamine (—CH$_2$—N(J)-O—), hydroxylimine (—CH=N—O—), and hydrazinyl (—CH$_2$—N(H)—N(H)—).

In each of the foregoing substructures relating to internucleoside linkages, J denotes a substituent group which is commonly hydrogen or an alkyl group or a more complicated group that varies from one type of linkage to another.

In addition to linking groups as described above that involve the modification or substitution of the —O—P—

O— atoms of a naturally occurring linkage, included within the scope of the present invention are linking groups that include modification of the 5'-methylene group as well as one or more of the —O—P—O— atoms. Linkages of this type are well documented in the prior art and include without limitation the following: amides (—CH$_2$—CH$_2$—N(H)—C(O)) and —CH$_2$—O—N═CH—; and alkylphosphorus (—C(J)$_2$-P(═O)(OJ)-C(J)$_2$-C(J)$_2$—). J is as described above.

Synthetic schemes for the synthesis of the substitute internucleoside linkages described above are disclosed in: U.S. Pat. Nos. 5,466,677; 5,034,506; 5,124,047; 5,278,302; 5,321,131; 5,519,126; 4,469,863; 5,455,233; 5,214,134; 5,470,967; 5,434,257. Additional background information relating to internucleoside linkages can be found in: WO 91/08213; WO 90/15065; WO 91/15500; WO 92/20822; WO 92/20823; WO 91/15500; WO 89/12060; EP 216860; PCT/US 92/04294; PCT/US 90/03138; PCT/US 91/06855; PCT/US 92/03385; PCT/US 91/03680; U.S. application Ser. Nos. 07/990,848; 07/892,902; 07/806,710; 07/763,130; 07/690,786; Stirchak, E. P., et al., Nucleic Acid Res., 1989, 17, 6129-6141; Hewitt, J. M., et al., 1992, 11, 1661-1666; Sood, A., et al., J. Am. Chem. Soc., 1990, 112, 9000-9001; Vaseur, J. J. et al., J. Amer. Chem. Soc., 1992, 114, 4006-4007; Musichi, B., et al., J. Org. Chem., 1990, 55, 4231-4233; Reynolds, R. C., et al., J. Org. Chem., 1992, 57, 2983-2985; Mertes, M. P., et al., J. Med. Chem., 1969, 12, 154-157; Mungall, W. S., et al., J. Org. Chem., 1977, 42, 703-706; Stirchak, E. P., et al., J. Org. Chem., 1987, 52, 4202-4206; Coull, J. M., et al., Tet. Lett., 1987, 28, 745; and Wang, H., et al., Tet. Lett., 1991, 32, 7385-7388.

Phosphoramidites used in the synthesis of oligonucleotides are available from a variety of commercial sources (included are: Glen Research, Sterling, Va.; Amersham Pharmacia Biotech Inc., Piscataway, N.J.; Cruachem Inc., Aston, Pa.; Chemgenes Corporation, Waltham, Mass.; Proligo LLC, Boulder, Colo.; PE Biosystems, Foster City Calif.; Beckman Coulter Inc., Fullerton, Calif.). These commercial sources sell high purity phosphoramidites generally having a purity of better than 98%. Those not offering an across the board purity for all amidites sold will in most cases include an assay with each lot purchased giving at least the purity of the particular phosphoramidite purchased. Commercially available phosphoramidites are prepared for the most part for automated DNA synthesis and as such are prepared for immediate use for synthesizing desired sequences of oligonucleotides. Phosphoramidites may be prepared by methods disclosed by e.g. Caruthers et al. (U.S. Pat. Nos. 4,415,732; 4,458,066; 4,500,707; 4,668,777; 4,973,679; and 5,132,418) and Köster et al. (U.S. Pat. No. Re. 34,069).

Oligonucleotides are generally prepared, as described above, on a support medium, e.g. a solid support medium. In general a first synthon (e.g. a monomer, such as a nucleoside) is first attached to a support medium, and the oligonucleotide is then synthesized by sequentially coupling monomers to the support-bound synthon. This iterative elongation eventually results in a final oligomeric compound or other polymer such as a polypeptide. Suitable support media can be soluble or insoluble, or may possess variable solubility in different solvents to allow the growing support bound polymer to be either in or out of solution as desired. Traditional support media such as solid supports are for the most part insoluble and are routinely placed in reaction vessels while reagents and solvents react with and/or wash the growing chain until the oligomer has reached the target length, after which it is cleaved from the support and, if necessary further worked up to produce the final polymeric compound. More recent approaches have introduced soluble supports including soluble polymer supports to allow precipitating and dissolving the iteratively synthesized product at desired points in the synthesis (Gravert et al., Chem. Rev., 1997, 97, 489-510).

The term support media is intended to include all forms of support known to the art skilled for the synthesis of oligomeric compounds and related compounds such as peptides. Some representative support media that are amenable to the methods of the present invention include but are not limited to the following: controlled pore glass (CPG); oxalyl-controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, Angew. Chem. Internal. Ed. 1972, 11, 314, sold under the trademark "PORASIL E" by Waters Associates, Framingham, Mass., USA); the mono ester of 1,4-dihydroxymethylbenzene and silica (see Bayer and Jung, Tetrahedron Lett., 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix or POROS, a copolymer of polystyrene/divinylbenzene (available from Perceptive Biosystems); soluble support media, polyethylene glycol PEG's (see Bonora et al., Organic Process Research & Development, 2000, 4, 225-231).

Further support media amenable to the present invention include without limitation PEPS support a polyethylene (PE) film with pendant long-chain polystyrene (PS) grafts (molecular weight on the order of $10^6$, (see Berg, et al., J. Am. Chem. Soc., 1989, 111, 8024 and International Patent Application WO 90/02749),). The loading capacity of the film is as high as that of a beaded matrix with the additional flexibility to accomodate multiple syntheses simultaneously. The PEPS film may be fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. Also, experiments with other geometries of the PEPS polymer such as, for example, non-woven felt, knitted net, sticks or microwellplates have not indicated any limitations of the synthetic efficacy.

Further support media amenable to the present invention include without limitation particles based upon copolymers of dimethylacrylamide cross-linked with N,N'-bisacryloyl-ethylenediamine, including a known amount of N-tertbutoxycarbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl safcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., J. Am. Chem. Soc., 1975, 97, 6584, Bioorg. Chem. 1979, 8, 351, and J. C. S. Perkin I 538 (1981)).

Further support media amenable to the present invention include without limitation a composite of a resin and another material that is also substantially inert to the organic synthesis reaction conditions employed. One exemplary composite (see Scott, et al., *J. Chrom. Sci.*, 1971, 9, 577) utilizes glass particles coated with a hydrophobic, cross-linked styrene polymer containing reactive chloromethyl groups, and is supplied by Northgate Laboratories, Inc., of Hamden, Conn., USA. Another exemplary composite contains a core of fluorinated ethylene polymer onto which has been grafted polystyrene (see Kent and Merrifield, *Israel J. Chem.* 1978, 17, 243 and van Rietschoten in *Peptides* 1974, Y. Wolman, Ed., Wiley and Sons, New York, 1975, pp. 113-116). Contiguous solid supports other than PEPS, such as cotton sheets (Lebl and Eichler, *Peptide Res.* 1989, 2, 232) and hydroxypropylacrylate-coated polypropylene membranes (Daniels, et al., *Tetrahedron Lett.* 1989, 4345). Acrylic acid-grafted polyethylene-rods and 96-microtiter wells to immobilize the growing peptide chains and to perform the compartmentalized synthesis. (Geysen, et al., *Proc. Natl. Acad. Sci. USA*, 1984, 81, 3998). A "tea bag" containing traditionally-used polymer beads. (Houghten, *Proc. Natl. Acad. Sci. USA*, 1985, 82, 5131). Simultaneous use of two different supports with different densities (Tregear, *Chemistry and Biology of Peptides*, J. Meienhofer, ed., Ann Arbor Sci. Publ., Ann Arbor, 1972 pp. 175-178). Combining of reaction vessels via a manifold (Gorman, *Anal. Biochem.*, 1984, 136, 397). Multicolumn solid-phase synthesis (e.g., Krchnak, et al., *Int. J. Peptide Protein Res.*, 1989, 33, 209), and Holm and Meldal, in "Proceedings of the 20th European Peptide Symposium", G. Jung and E. Bayer, eds., Walter de Gruyter & Co., Berlin, 1989 pp. 208-210). Cellulose paper (Eichler, et al., *Collect. Czech. Chem. Commun.*, 1989, 54, 1746). Support mediated synthesis of peptides have also been reported (see, *Synthetic Peptides: A User's Guide*, Gregory A. Grant, Ed. Oxford University Press 1992; U.S. Pat. Nos. 4,415,732; 4,458,066; 4,500,707; 4,668,777; 4,973,679; 5,132,418; 4,725,677 and Re-34,069.)

Support bound oligonucleotide synthesis relies on sequential addition of nucleotides to one end of a growing chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725, 677 and U.S. Pat. No. Re. 34,069.

Commercially available equipment routinely used for the support media based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

In general, the phosphorus protecting group (pg) is an alkoxy or alkylthio group or O or S having a β-eliminable group of the formula —$CH_2CH_2$-$G_w$, wherein $G_w$ is an electron-withdrawing group. Suitable examples of pg that are amenable to use in connection with the present invention include those set forth in the Caruthers U.S. Pat. Nos. 4,415,732; 4,458,066; 4,500,707; 4,668,777; 4,973,679; and 5,132,418; and Köster U.S. Pat. Nos. 4,725,677 and U.S. Pat. No. Re. 34,069. In general the alkyl or cyanoethyl withdrawing groups are preferred, as commercially available phosphoramidites generally incorporate either the methyl or cyanoethyl phosphorus protecting group.

The method for removal of pg depends upon the specific pg to be removed. The β-eliminable groups, such as those disclosed in the Köster et al. patents, are generally removed in a weak base solution, whereby an acidic β-hydrogen is extracted and the —$CH_2CH_2$-$G_w$ group is eliminated by rearrangement to form the corresponding acrylo-compound $CH_2$=CH—$G_w$. In contrast, an alkyl group is generally removed by nucleophilic attack on the α-carbon of the alkyl group. Such PGs are described in the Caruthers et al. patents, as cited herein.

The person skilled in the art will recognize that oxidation of P(III) to P(V) can be carried out by a variety of reagents. Furthermore, the person skilled in the art will recognize that the P(V) species can exist as phosphate triesters, phosphorothioate diesters, or phosphorodithioate diesters. Each type of P(V) linkage has uses and advantages, as described herein. Thus, the term "oxidizing agent" should be understood broadly as being any reagent capable of transforming a P(III) species (e.g. a phosphite) into a P(V) species. Thus the term "oxidizing agent" includes "sulfurizing agent," which is also considered to have the same meaning as "thiation reagent." Oxidation, unless otherwise modified, indicates introduction of oxygen or sulfur, with a concomitant increase in P oxidation state from III to V. Where it is important to indicate that an oxidizing agent introduces an oxygen into a P(III) species to make a P(V) species, the oxidizing agent will be referred to herein is "an oxygen-introducing oxidizing reagent."

Oxidizing reagents for making phosphate diester linkages (i.e. oxygen-introducing oxidizing reagents) under the phosphoramidite protocol have been described by e.g. Caruthers et al. and Köster et al., as cited herein. Examples of sulfurization reagents which have been used to synthesize oligonucleotides containing phosphorothioate bonds include elemental sulfur, dibenzoyltetrasulfide, 3-H-1,2-benzidithiol-3-one 1,1-dioxide (also known as Beaucage reagent), tetraethylthiuram disulfide (TETD), and bis(O,O-diisopropoxy phosphinothioyl) disulfide (known as Stec reagent). Oxidizing reagents for making phosphorothioate diester linkages include phenylacetyldisulfide (PADS), as described by Cole et al. in U.S. Pat. No. 6,242,591. In some embodiments of the invention, the phosphorothioate diester and phosphate diester linkages may alternate between sugar subunits. In other embodiments of the present invention, phosphorothioate linkages alone may be employed. In some embodiments, the thiation reagent may be a dithiuram disulfides. See U.S. Pat. No. 5,166,387 for disclosure of some suitable dithiuram disulfides. It has been surprisingly found that one dithiuram disulfide may be used together with a standard capping reagent, so that capping and oxidation may be conducted in the same step. This is in contrast to standard oxidative reagents, such as Beaucage reagent, which require that capping and oxidation take place in separate steps, generally including a column wash between steps.

The 5'-protecting group bg or T''' is a protecting group that is orthogonal to the protecting groups used to protect the nucleobases, and is also orthogonal, where appropriate to 2'-O-protecting groups, as well as to the 3'-linker to the solid support. In some embodiments of the invention, the 5'-protecting group is acid labile. In some embodiments according to the invention, the 5'-protecting group is selected from an optionally substituted trityl group and an optionally substituted pixyl group. In some embodiments, the pixyl group is substituted with one or more substituents selected from alkyl, alkoxy, halo, alkenyl and alkynyl groups. In some embodiments, the trityl groups are substituted with from about 1 to about 3 alkoxy groups, specifically about 1 to about 3 methoxy groups. In particular embodiments of the invention, the trityl groups are substituted with 1 or 2 methoxy groups at the 4- and (if applicable) 4'-positions. A particularly acceptable trityl group is 4,4'-dimethoxytrityl (DMT or DMTr).

In the context of the present invention, the term "reagent push" has the meaning of a volume of solvent that is substantially free of any active compound (i.e. reagent, activator, by-product, or other substance other than solvent), which volume of solvent is introduced to the column for the purpose, and with the effect, of pushing a reagent solution onto and through the column ahead of a subsequent reagent solution. A reagent push need not be an entire column volume, although in some cases it may include one or more column volumes. In some embodiments, a reagent push comprises at least the minimum volume necessary to substantially clear reagent, by-products and/or activator from a cross-section of the column immediately ahead of the front formed by the reagent solution used for the immediately subsequent synthetic step. An active compound, whether a reagent, by-product or activator, is considered substantially cleared if the concentration of the compound in a cross-section of the column at which the following reagent solution front is located, is low enough that it does not substantially affect the activity of the following reagent solution. The person skilled in the art will recognize that this the volume of solvent required for a "reagent push" will vary depending upon the solvent, the solubility in the solvent of the reagents, activators, by-products, etc., that are on the column, the amounts of reagents, activators, by-products, etc. that are to be cleared from the column, etc. It is considered within the skill of the artisan to select an appropriate volume for each reagent push, especially with an eye toward the Examples, below.

As used herein, unless "column wash" is otherwise modified, it has the same meaning as "reagent push." In some embodiments of the invention, column wash may imply that at least one column volume is permitted to pass through the column before the subsequent reagent solution is applied to the column. Where a column volume (CV) of the column wash is specified, this indicates that a volume of solvent equivalent to the interior volume of the unpacked column is used for the column wash.

In the context of the present invention, a solvent wash is a solvent containing substantially no active compound that is applied to a column between synthetic steps. A "wash step" is a step in which a solvent wash is applied to the column. Both "reagent push" and "column wash" are included within this definition of "wash step".

A solvent wash may be a pure chemical compound or a mixture of chemical compounds, the solvent being capable of dissolving an active compound.

In some embodiments according to the present invention, a solvent wash used in one of the wash steps may comprise some percentage of acetonitrile, not to exceed 50% v/v.

The capping step may be accomplished with an art-recognized capping protocol, such as one provided by the primer-support vendor, etc. Suitable capping reagents are set forth in the Examples, below.

The sequence of capping and oxidation steps may be reversed, if desired. That is, capping may precede or follow oxidation. Also, with selection of a suitable thiation reagent, the oxidation and capping steps may be combined into a single step. For example, it has been surprisingly found that capping with acetic anhydride may be conducted in the presence of N,N'-dimethyldithiuram disulfide.

Various solvents may be used in the oxidation reaction. Suitable solvents are identified in the Caruthers et al. and Köster et al. patents, cited herein. The Cole et al. patent describes acetonitrile as a solvent for phenylacetyldisulfide. Other suitable solvents include toluene, xanthenes, dichloromethane, etc.

Reagents for cleaving an oligonucleotide from a support are set forth, for example, in the Caruthers et al. and Köster et al. patents, as cited herein. It is considered good practice to cleave oligonucleotide containing thymidine (T) nucleotides in the presence of an alkylated amine, such as triethylamine, when the phosphorus protecting group is O—$CH_2CH_2CN$, because this is now known to avoid the creation if cyano-ethylated thymidine nucleotides (CNET). Avoidance of CNET adducts is described in general in U.S. Pat. No. 6,465,628, which is incorporated herein by reference, and especially the Examples in columns 20-30, which are specifically incorporated by reference.

The oligonucleotide may be worked up by standard procedures known in the art, for example by size exclusion chromatography, high performance liquid chromatography (e.g. reverse-phase HPLC), differential precipitation, etc. In some embodiments according to the present invention, the oligonucleotide is cleaved from a solid support while the 5'-OH protecting group is still on the ultimate nucleoside. This so-called DMT-on (or trityl-on) oligonucleotide is then subjected to chromatography, after which the DMT group is removed by treatment in an organic acid, after which the oligonucleotide is de-salted and further purified to form a final product.

The 5'-hydroxyl protecting groups may be any groups that are selectively removed under suitable conditions. In particular, the 4,4'-dimethoxytriphenylmethyl (DMT) group is a favored group for protecting at the 5'-position, because it is readily cleaved under acidic conditions (e.g. in the presence of dichloroacetic acid (DCA), trichloroacetic acid (TCA), or acetic acid. Removal of DMT from the support-bound oligonucleotide is generally performed with DCA (e.g. about 3 to about 10 percent DCA (v/v) in a suitable solvent. Removal of oligonucleotide after cleavage from the support is generally performed with acetic acid.

As described herein, oligonucleotides can be prepared as chimeras with other oligomeric moieties. In the context of this invention, the term "oligomeric compound" refers to a polymeric structure capable of hybridizing a region of a nucleic acid molecule, and an "oligomeric moiety" a portion of such an oligomeric compound. Oligomeric compounds include oligonucleotides, oligonucleosides, oligonucleotide analogs, modified oligonucleotides and oligonucleotide mimetics. Oligomeric compounds can be linear or circular, and may include branching. They can be single stranded or double stranded, and when double stranded, may include overhangs. In general an oligomeric compound comprises a backbone of linked monomeric subunits where each linked monomeric subunit is directly or indirectly attached to a heterocyclic base moiety. The linkages joining the monomeric subunits, the monomeric subunits and the heterocyclic base moieties can be variable in structure giving rise to a plurality of motifs for the resulting oligomeric compounds including hemimers, gapmers and chimeras. As is known in the art, a nucleoside is a base-sugar combination. The base portion of the nucleoside is normally a heterocyclic base moiety. The two most common classes of such heterocyclic bases are purines and pyrimidines. In the context of this invention, the term "oligonucleoside" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

As used herein, the term nucleoside means a sugar covalently bonded to a nucleobase. A modified nucleoside is a nucleoside that has been covalently altered in some way, e.g. by removal of an OH group (e.g. 2'-deoxy nucleosides), by addition of a 2'-substituent (e.g. 2'-O-substituents, LNA's, etc.), by modification of a base (e.g. by addition of one or more substituents on a base, such as 5'-methyl cytosine, by replacing a cyclic nitrogen with a carbon, vice versa or both, etc.) A nucleoside mimetic is a moiety that either lacks a sugar ring or has what cannot be properly called a sugar ring (e.g. a morphonlino group), but nonetheless performs the function of holding a nucleobase (whether naturally occurring or modified) in a position amenable to specific hybridization.

The term phosphate refers to P(V), as depicted below:

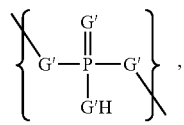

wherein each G', independently of the others, is either O or S, G'H may exist in its ionized form, and the brackets { } indicate where the phosphate is covalently linked to a nucleoside, substituted nucleoside or nucleoside mimetic ring. The person skilled in the art will recognize that "phospho diester" has the art-recognized meaning of:

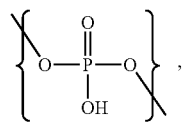

wherein the brackets have the same meaning as above, whereas phosphorothioate diester (or simply phosphorothioate) means:

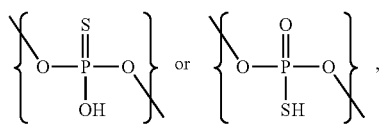

the two forms being tautomeric with one another, and the term phosphorodithioate diester (or simply phosphorodithioate) means:

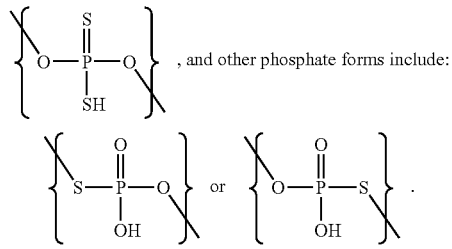, and other phosphate forms include:

Representative United States patents that teach the preparation of oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In the context of this invention, the term "oligonucleotide mimetic" refers to an oligonucleotide wherein the backbone of the nucleotide units has been replaced with novel groups. Although the term is intended to include oligomeric compounds wherein only the furanose ring or both the furanose ring and the internucleotide linkage are replaced with novel groups, replacement of only the furanose ring is also referred to in the art as being a sugar surrogate. Oligonucleotide mimetics can be further modified to incorporate one or more modified heterocyclic base moieties to enhance properties such as hybridization.

One oligonucleotide mimetic that has been reported to have excellent hybridization properties, is peptide nucleic acids (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., Science, 1991, 254, 1497-1500.

PNA has been modified to incorporate numerous modifications since the basic PNA structure was first prepared. The basic structure is shown below:

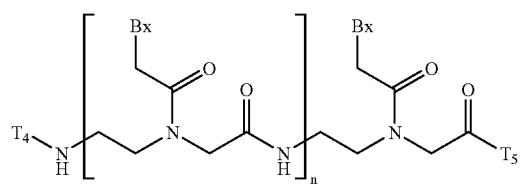

wherein

Bx is a heterocyclic base moiety;

$T_4$ is is hydrogen, an amino protecting group, —C(O)R$_5$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

$T_5$ is —OH, —N($Z_1$)$Z_2$, $R_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

$Z_1$ is hydrogen, $C_1$-$C_6$ alkyl, or an amino protecting group;

$Z_2$ is hydrogen, $C_1$-$C_6$ alkyl, an amino protecting group, —C(=O)—(CH$_2$)$_n$-J-$Z_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —$C_1$-$C_6$ alkyl, —C(=O)—CH$_3$, benzyl, benzoyl, or —(CH$_2$)$_n$—N(H)$Z_1$;

each J is O, S or NH;

$R_5$ is a carbonyl protecting group; and n is from 2 to about 50.

Another class of oligonucleotide mimetic that has been studied is based on linked morpholino units (morpholino nucleic acids) having heterocyclic base moieties attached to the morpholino ring. There are a number of linking groups reported that are used to link the morpholino rings. A preferred class of linking groups were selected as being non-ionic. The non-ionic morpholino-based oligomeric compounds are less likely to have undesired interactions with cellular proteins (Dwaine A. Braasch and David R. Corey, Biochemistry, 2002, 41(14), 4503-4510). Morpholino-based oligomeric compounds are disclosed in U.S. Pat. No. 5,034,506, issued Jul. 23, 1991.

The morpholino class of oligomeric compounds have been prepared having a variety of different linking groups ($L_2$) joining the monomeric subunits. The formula of the basic morpholino oligomeric compound is shown below:

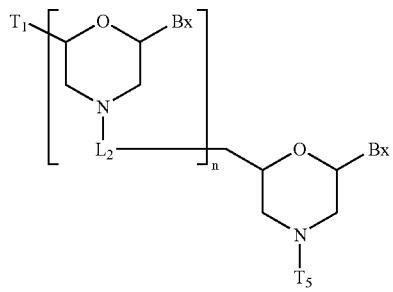

wherein $T_1$ is hydroxyl or a protected hydroxyl;

$T_5$ is hydrogen or a phosphate or phosphate derivative;

$L_2$ is a linking group; and n is from 2 to about 50.

Another class of oligonucleotide mimetic that has been studied is based on linked morpholino units having heterocyclic bases attached to the morpholino ring. Morpholino-based oligomeric compounds are non-ionic mimics of oligonucleotides which are less likely to form undesired interactions with cellular proteins (Dwaine A. Braasch and David R. Corey, Biochemistry, 2002, 41(14), 4503-4510). Morpholino-based oligomeric compounds are disclosed in U.S. Pat. No. 5,034,506, issued Jul. 23, 1991.

The morpholino class of oligomeric compounds have been prepared having a variety of different linking groups joining the monomeric subunits. The formula of the basic morpholino oligomeric compound is shown below:

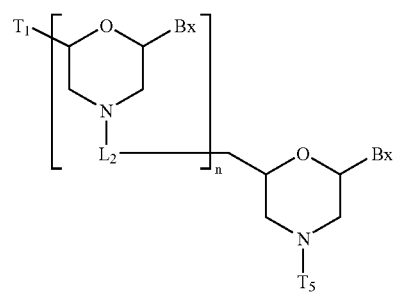

wherein $T_1$ is hydroxyl or a protected hydroxyl;

$T_5$ is hydrogen or a phosphate or phosphate derivative;

$L_2$ is a linking group; and n is from 2 to about 50.

A further class of oligonucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate E. Coli RNase resulting in cleavage of the target RNA strand.

The general formula of CeNA is shown below:

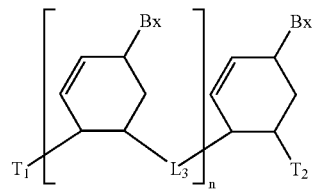

wherein each Bx is a heterocyclic base moiety;

$T_1$ is hydroxyl or a protected hydroxyl; and $T_2$ is hydroxyl or a protected hydroxyl.

Another class of oligonucleotide mimetic is referred to as phosphonomonoester nucleic acids which in one aspect have a similarity to PNA but incorporate a phosphorus group in the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below along with one selection of Markush variables which give a compound having a resemblance to PNA.

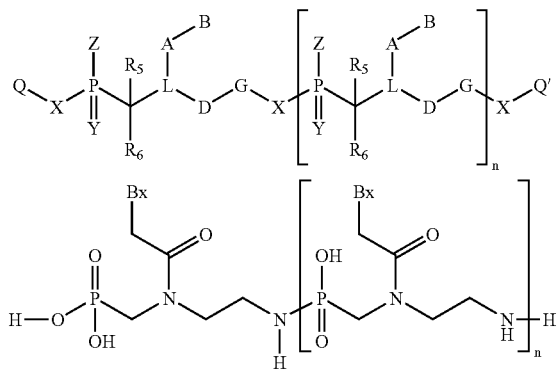

The term "nucleobase," as used herein, is intended to by synonymous with "nucleic acid base or mimetic thereof" as herein described. In general, a nucleobase is any substructure that contains one or more atoms or groups of atoms capable of hydrogen bonding to a base of an oligonucleotide. Thus, the term "nucleobase" encompasses naturally-occurring nucleobases, i.e. the naturally-occurring purines and pyrimidines (guanine, adenine, thymine, cytidine and uracil), as well as protected analogs thereof and a wide variety of mimetic moieties as described herein.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH₃) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]beinzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. Nos. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present invention involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553), cholic acid (Manoharan et al., Bioorg. Med. Chem. Lett., 1994, 4, 1053), a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651), a palmityl moiety (Mishra et al., Biochim. Biophys. Acta, 1995, 1264, 229), or an octadecylamine or hexylaminocarbonyl-oxycholesterol moiety (Crooke et al., J. Pharmacol. Exp. Ther., 1996, 277, 923).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned, and each of which is herein incorporated by reference.

In one aspect of the present invention oligomeric compounds are prepared having polycyclic heterocyclic compounds in place of one or more heterocyclic base moieties. A number of tricyclic heterocyclic comounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

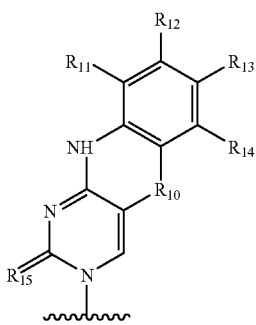

Representative cytosine analogs that make 3 hydrogen bonds with a guanosine in a second strand include 1,3-diazaphenoxazine-2-one ($R_{10}$=O, $R_{11}$-$R_{14}$=H) [Kurchavov, et al., *Nucleosides and Nucleotides*, 1997, 16, 1837-1846], 1,3-diazaphenothiazine-2-one ($R_{10}$=S, $R_{11}$-$R_{14}$=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one ($R_{10}$=O, $R_{11}$-$R_{14}$=F) [Wang, J.; Lin, K.-Y., Matteucci, M. Tetrahedron Lett. 1998, 39, 8385-8388]. Incorporated into oligo-nucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155,920; and U.S. patent application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—$(CH_2)_2$—$NH_2$, $R_{12-14}$=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a $\Delta T_m$ of up to 18° relative to 5-methyl cytosine ($dC5^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to $dC5^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. patent Ser. No. 6,028,183, which issued on May 22, 2000, and U.S. patent Ser. No. 6,007,992, which issued on Dec. 28, 1999, the contents of both are commonly assigned with this application and are incorporated herein in their entirety. Such compounds include those having the formula:

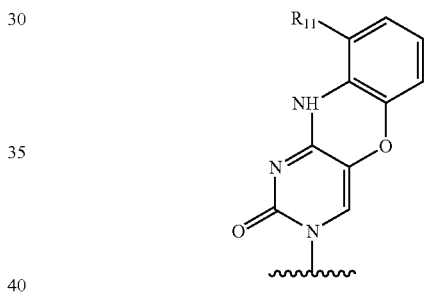

Wherein $R_{11}$ includes $(CH_3)_2N$—$(CH_2)_2$—O—; $H_2N$—$(CH_2)_3$—; Ph-$CH_2$—O—C(=O)—N(H)—$(CH_2)_3$—; $H_2N$—; Fluorenyl-$CH_2$—O—C(=O)—N(H)—$(CH_2)_3$—; Phthalimidyl-$CH_2$—O—C(=O)—N(H)—$(CH_2)_3$—; Ph-$CH_2$—O—C(=O)—N(H)—$(CH_2)_2$—O—; Ph-$CH_2$—O—C(=O)—N(H)—$(CH_2)_3$—O—; $(CH_3)_2N$—N(H)—$(CH_2)_2$—O—; Fluorenyl-$CH_2$—O—C(=O)—N(H)—$(CH_2)_2$—O—; Fluorenyl-$CH_2$—O—C(=O)—N(H)—$(CH_2)_3$—O—; $H_2N$—$(CH_2)_2$—O—$CH_2$—; $N_3$—$(CH_2)_2$—O—$CH_2$—; $H_2N$—$(CH_2)_2$—O—, and $NH_2C$(=NH)NH—.

Also disclosed are tricyclic heterocyclic compounds of the formula:

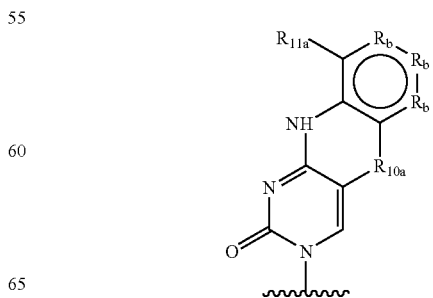

Wherein $R_{10a}$ is O, S or N—CH$_3$;

$R_{11a}$ is $A(Z)_{x1}$, wherein A is a spacer and Z independently is a label bonding group bonding group optionally bonded to a detectable label, but $R_{11a}$ is not amine, protected amine, nitro or cyano;

X1 is 1, 2 or 3; and $R_b$ is independently —CH=, —N=, —C(C$_{1-8}$ alkyl)= or —C(halogen)=, but no adjacent $R_b$ are both —N=, or two adjacent $R_b$ are taken together to form a ring having the structure:

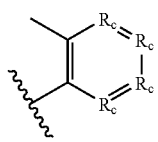

where $R_c$ is independently —CH=, —N=, —C(C$_{1-8}$ alkyl)= or —C(halogen)=, but no adjacent $R_b$ are both —N=.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K.-Y.; Matteucci, M. J. Am. Chem. Soc. 1998, 120, 8531-8532]. The activity enhancement was even more pronounced in case of G-clamp, as a single substitution was shown to significantly improve the in vitro potency of a 20 mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligonucleotide design and to better understand the impact of these heterocyclic modifications on the biological activity, it is important to evaluate their effect on the nuclease stability of the oligomers.

Further tricyclic and tetracyclic heteroaryl compounds amenable to the present invention include those having the formulas:

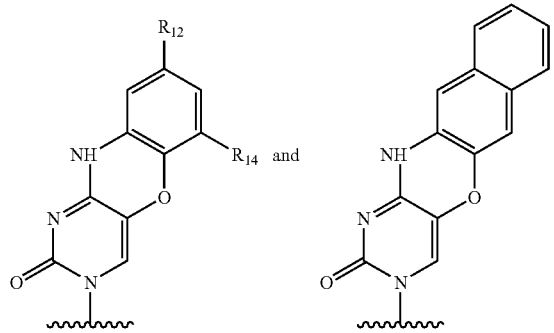

wherein $R_{14}$ is NO$_2$ or both $R_{14}$ and $R_{12}$ are independently —CH$_3$. The synthesis of these compounds is dicslosed in U.S. patent Ser. No. 5,434,257, which issued on Jul. 18, 1995, U.S. patent Ser. No. 5,502,177, which issued on Mar. 26, 1996, and U.S. patent Ser. No. 5,646,269, which issued on Jul. 8, 1997, the contents of which are commonly assigned with this application and are incorporated herein in their entirety.

Further tricyclic heterocyclic compounds amenable to the present invention also disclosed in the "257, 177 and 269" Patents include those having the formula:

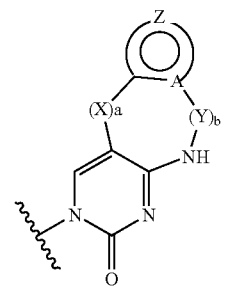

a and b are independently 0 or 1 with the total of a and b being 0 or 1;

A is N, C or CH;

X is S, O, C=O, NH or NCH$_2$, R$^6$;

Y is C=O;

Z is taken together with A to form an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a C atom, 2 N ring heteroatoms separated by a carbon atom, or 3 N ring heteroatoms at least 2 of which are separated by a carbon atom, and wherein the aryl or heteroaryl ring carbon atoms are unsubstituted with other than H or at least 1 nonbridging ring carbon atom is fubstituted with R$^{20}$ or =O;

or Z is taken together with A to form an aryl ring structure comprising 6 ring atoms wherein the aryl ring carbon atoms are unsubstituted with other than H or at least 1 nonbridging ring carbon atom is substituted with R$^6$ or =O;

R$^6$ is independently H, C$_{1-6}$ alkyl, C$_{2-6}$ alkenyl, C$_{2-6}$ alkynyl, NO$_2$, N(R$^3$)$_2$, CN or halo, or an R$^6$ is taken together with an adjacent Z group R$^6$ to complete a phenyl ring;

R$^{20}$ is, independently, H, C$_{1-6}$ alkyl, C$_{2-6}$ alkyl, C$_{2-6}$ alkenyl, C$_{2-6}$ alkynyl, NO$_2$, N(R$^{21}$)$_2$, CN, or halo, or an R$^{20}$ is taken together with an adjacent R$^{20}$ to complete a ring containing 5 or 6 ring atoms, and tautomers, solvates and salts thereof;

R$^{21}$ is, independently, H or a protecting group;

R$^3$ is a protecting group or H; and tautomers, solvates and salts thereof.

More specific examples included in the "257, 177 and 269" Patents are compounds of the formula:

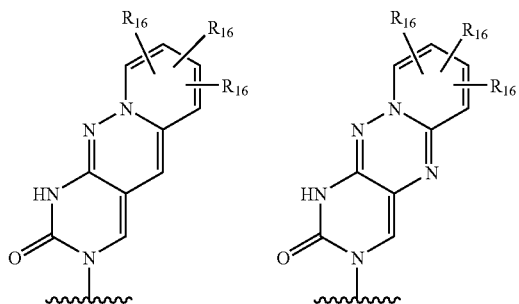
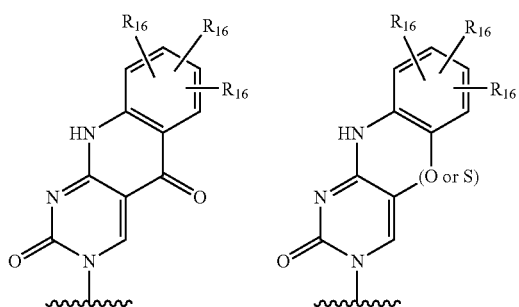
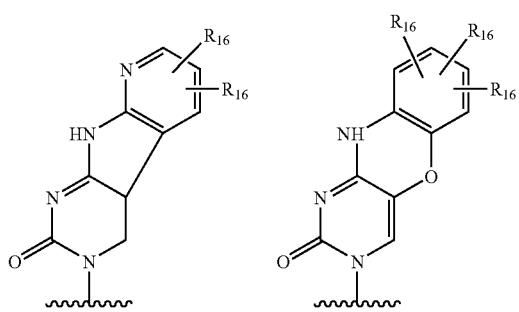
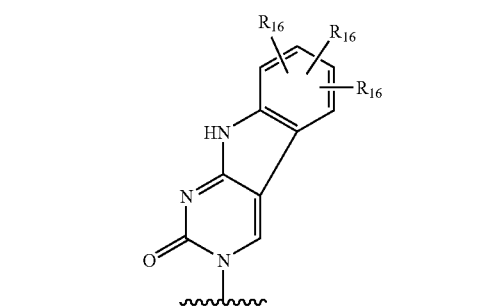
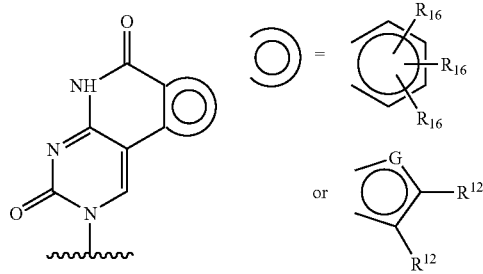

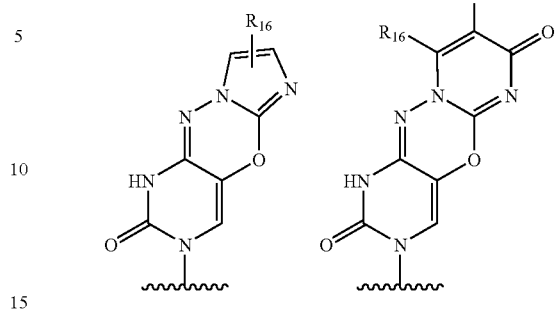

-continued wherein each $R_{16}$, is, independently, selected from hydrogen and various substituent groups.

Further polycyclic base moieties having the formula:

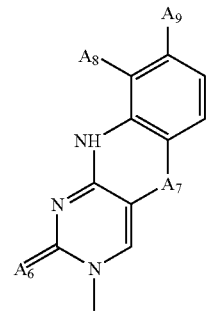

wherein:

$A_6$ is O or S;

$A_7$ is $CH_2$, N—$CH_3$, O or S;

each $A_8$ and $A_9$ is hydrogen or one of $A_8$ and $A_9$ is hydrogen and the other of $A_8$ and $A_9$ is selected from the group consisting of:

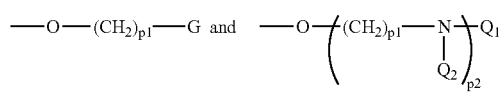

wherein:

wherein:

G is —CN, —$OA_{10}$, —$SA_{10}$, —N(H)$A_{10}$, —ON(H)$A_{10}$ or —C(=NH)N(H)$A_{10}$;

$Q_1$ is H, —$NHA_{10}$, —C(=O)N(H)$A_{10}$, —C(=S)N(H)$A_{10}$ or —C(=NH)N(H)$A_{10}$;

each $Q_2$ is, independently, H or Pg;

$A_{10}$ is H, Pg, substituted or unsubstituted $C_1$-$C_{10}$ alkyl, acetyl, benzyl, —$(CH_2)_{p3}NH_2$, —$(CH_2)_{p3}N(H)Pg$, a D or L α-amino acid, or a peptide derived from D, L or racemic α-amino acids;

Pg is a nitrogen, oxygen or thiol protecting group;
each p1 is, independently, from 2 to about 6;
p2 is from 1 to about 3; and
p3 is from 1 to about 4;

are disclosed in U.S. patent application Ser. No. 09/996,292 filed Nov. 28, 2001, which is commnonly owned with the instant application, and is herein incorporated by reference.

Exemplary preferred antisense compounds include DNA or RNA sequences that comprise at least the 8 consecutive nucleobases from the 5'-terminus of one of the illustrative preferred antisense compounds (the remaining nucleobases being a consecutive stretch of the same DNA or RNA beginning immediately upstream of the 5'-terminus of the antisense compound which is specifically hybridizable to the target nucleic acid and continuing until the DNA or RNA contains about 8 to about 80 nucleobases). Similarly preferred antisense compounds are represented by DNA or RNA sequences that comprise at least the 8 consecutive nucleobases from the 3'-terminus of one of the illustrative preferred antisense compounds (the remaining nucleobases being a consecutive stretch of the same DNA or RNA beginning immediately downstream of the 3'-terminus of the antisense compound which is specifically hybridizable to the target nucleic acid and continuing until the DNA or RNA contains about 8 to about 80 nucleobases). One having skill in the art, once armed with the empirically-derived preferred antisense compounds illustrated herein will be able, without undue experimentation, to identify further preferred antisense compounds.

Antisense and other compounds of the invention, which hybridize to the target and inhibit expression of the target, are identified through experimentation, and representative sequences of these compounds are herein identified as preferred embodiments of the invention. While specific sequences of the antisense compounds are set forth herein, one of skill in the art will recognize that these serve to illustrate and describe particular embodiments within the scope of the present invention. Additional preferred antisense compounds may be identified by one having ordinary skill.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U. S. A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (reviewed in To, *Comb. Chem. High Throughput Screen*, 2000, 3, 235-41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a particular protein. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding a particular protein, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. mRNA transcripts produced via the process of splicing of two (or more) mRNAs from different gene sources are known as "fusion transcripts". It has also been found that introns can be effective, and therefore preferred, target regions for antisense compounds targeted, for example, to DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and extronic regions.

Upon excision of one or more exon or intron regions or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable.

An antisense compound is specifically hybridizable when binding of the compound to the target DNA or RNA molecule interferes with the normal function of the target DNA or RNA to cause a loss of activity, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed. It is preferred that the antisense compounds of the present invention comprise at least 80% sequence complementarity with the target nucleic acid, more that they comprise 90% sequence complementarity and even more comprise 95% sequence complementarity with the target nucleic acid sequence to which they are targeted. Percent complementarity of an antisense compound with a target nucleic acid can be determined routinely using basic local alignment search tools (BLAST programs) (Altschul et al., *J. Mol. Biol.*, 1990, 215, 403-410; Zhang and Madden, *Genome Res.*, 1997, 7, 649-656).

Antisense and other compounds of the invention, which hybridize to the target and inhibit expression of the target, are identified through experimentation, and representative sequences of these compounds are hereinbelow identified as preferred embodiments of the invention. The sites to which these preferred antisense compounds are specifically hybridizable are hereinbelow referred to as "preferred target regions" and are therefore preferred sites for targeting. As used herein the term "preferred target region" is defined as at least an 8-nucleobase portion of a target region to which an active antisense compound is targeted. While not wishing to be bound by theory, it is presently believed that these target regions represent regions of the target nucleic acid which are accessible for hybridization.

While the specific sequences of particular preferred target regions are set forth below, one of skill in the art will recognize that these serve to illustrate and describe particular embodiments within the scope of the present invention. Additional preferred target regions may be identified by one having ordinary skill.

Target regions 8-80 nucleobases in length comprising a stretch of at least eight (8) consecutive nucleobases selected from within the illustrative preferred target regions are considered to be suitable preferred target regions as well.

Exemplary good preferred target regions include DNA or RNA sequences that comprise at least the 8 consecutive nucleobases from the 5'-terminus of one of the illustrative preferred target regions (the remaining nucleobases being a consecutive stretch of the same DNA or RNA beginning immediately upstream of the 5'-terminus of the target region and continuing until the DNA or RNA contains about 8 to about 80 nucleobases). Similarly good preferred target regions are represented by DNA or RNA sequences that comprise at least the 8 consecutive nucleobases from the 3'-terminus of one of the illustrative preferred target regions (the remaining nucleobases being a consecutive stretch of the same DNA or RNA beginning immediately downstream of the 3'-terminus of the target region and continuing until the DNA or RNA contains about 8 to about 80 nucleobases). One having skill in the art, once armed with the empirically-derived preferred target regions illustrated herein will be able, without undue experimentation, to identify further preferred target regions. In addition, one having ordinary skill in the art will also be able to identify additional compounds, including oligonucleotide probes and primers, that specifically hybridize to these preferred target regions using techniques available to the ordinary practitioner in the art.

The ability of oligonucleotides to bind to their complementary target strands is compared by determining the melting temperature ($T_m$) of the hybridization complex of the oligonucleotide and its complementary strand. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands. The structure-stability relationships of a large number of nucleic acid modifications have been reviewed (Freier and Altmann, Nucl. Acids Research, 1997, 25, 4429-443).

EXAMPLES

The present invention may be further appreciated upon reference to the following, non-limiting examples.

In the following examples, unless otherwise stated, the following solutions were used:

Deoxyadenosine amidite (dA amidite): 0.19 g/ml in acetonitrile.

Deoxyguanosine amidite (dG amidite): 0.19 g/ml in acetonitrile.

Deoxycytosine amidite (dC amidite): 0.19 g/ml in acetonitrile.

Deoxythymidine amidite (dT amidite): 0.17 g/ml in acetonitrile.

Toluene: Neat.

Acetonitrile: Neat.

Tetrazole (coupling activator): 0.030 g/ml in acetonitrile.

PADS (phenylacetyl disulfide, thiation reagent):
  PADS: 43.5 g phenyl acetyl disulfide and 3-picoline: 346 g 3-picoline in 283 g acetonitrile.

Capping Reagent A:
  Cap A: 149 g:
    Pyridine: 49 g, and
    N-methyl imidazole: 35 g in 66 g acetonitrile.

Capping Reagent B:
  Cap B: 141 g:
    Ac$_2$O: 36 g, in 105 g acetonitrile.

Triethylamine:
  58 g TEA in 63 g acetonitrile.

Example 1

80 mmole Solid Phase Synthesis of ISIS 2302

The following phosphorothioate oligodeoxyribonucleotide was prepared according to the procedures set forth below: ISIS 2303=5'-GCC-CAA-GCT-GGC-ATC-CGT-CA-3'.

Primer support having a loading value of 90 μmol/g was obtained, and the amount of primer support necessary to obtain 80 mmol of the 3'-terminal nucleoside attached to solid support was calculated to be 888.9 g of support. Support, 889.1 g, was weighed into a polypropylene container and 400-500 mL of acetonitrile per 100 g of support were added to produce a slurry. The support was then packed into a suitable column, which was attached to the Amersham OligoProcess synthesizer per established procedures. A new synthesis result directory was created to produce the sequence set forth above.

Deblock solution, activator solution, deoxyphosphoramidite solutions, thiation solution, capping solution A, capping solution B, triethylamine solution, acetonitrile and toluene were loaded into the appropriate reservoirs. The synthesis cycle was conducted as follows:
Detritylation: DCA in toluene;
Column wash: toluene;
Coupling: phosphoramidite in acetonitrile;
Acetonitrile push/wash;
Oxidation: phenyl acetyl disulfide in acetonitrile;
Acetonitrile push;
Capping: Reagent A;
Capping: Reagent B;
Toluene wash;

This cycle is repeated for each of the phosphoramidites to be coupled to the oligonucleotide. Synthesis completes with the final toluene wash.

Following completion of synthesis, the column was unpacked according to an established procedure and the contents of the column were transferred to a 10 L polypropylene container. Ammonium hydroxide solution, approximately 5,000 mL, was added to the support and stirred to form a slurry. The slurry was then evenly divided among ten graduated, 2 L glass bottles, each of which was then diluted with about 800-900 mL of additional ammonium hydroxide, refrigerated for three days (~5-10° C.) and then incubated at 50-60° C. for 23.5 h, after which they were again refrigerated. The cooled solutions were then decanted through a large Buchner funnel containing a filter paper (Whatman #4) into appropriate-sized clean glass bottles. Approximately 1 L of 50% water/purified ethanol (v/v) was then added to each bottle containing support. Each bottle was shaken to slurry, and then filtered as above.

The filtrate was next transferred to a mixing tank, to which was added approximately 114 mL of triethylamine (TEA). The initial solution weight was 16.5 kg. The solution was then mixed for approximately 10-20 minutes, after which the solution was centrated by vacuum to give a final solution weight of 7.9 kg. Approximately 60 mL of TEA were then added to the solution. The solution, about 10,000 ml, was then transferred into graduated bottles.

The O.D. per mL (1068.9 OD/ml) at 260 nm was then obtained and the impurity profile was otained by HPLC.

Table 1 contains the peak data for a reverse-phase HPLC chromatogram of the crude, trityl-on product.

TABLE 1

| # | Retention Time (min.) | Area (uV* sec) | Height (uV) | % of Total Area |
|---|---|---|---|---|
| 1 | 15.817 | 2634 | 248 | 0.11 |
| 2 | 16.117 | 2124 | 313 | 0.08 |
| 3 | 16.300 | 4040 | 450 | 0.16 |
| 4 | 16.733 | 3940 | 496 | 0.16 |
| 5 | 17.050 | 9021 | 690 | 0.36 |
| 6 | 17.400 | 4036 | 318 | 0.16 |
| 7 | 17.933 | 45284 | 3526 | 1.81 |
| 8 | 18.000 | 22453 | 3433 | 0.90 |
| 9 | 18.150 | 24904 | 3063 | 1.00 |
| 10 | 18.350 | 41182 | 4284 | 1.65 |
| 11 | 18.567 | 52335 | 6081 | 2.09 |
| 12 | 18.833 | 52706 | 4159 | 2.11 |
| 13 | 19.117 | 56015 | 6302 | 2.24 |
| 14 | 19.383 | 66716 | 6652 | 2.67 |
| 15 | 19.667 | 80493 | 7735 | 3.22 |
| 16 | 19.917 | 94194 | 8488 | 3.76 |
| 17 | 20.183 | 134702 | 12129 | 5.38 |
| 18 | 20.700 | 1792952 | 120874 | 71.66 |
| 19 | 25.583 | 3492 | 396 | 0.14 |
| 20 | 25.850 | 8818 | 912 | 0.35 |

Overall, 10,689,000 ODs of 71% full-length crude ISIS-2302 were obtained.

Example 2

0.75 mmole Synthesis of ISIS-3521

A procedure similar to that employed in Example 1, above, was followed for preparation of 0.75 mmole of ISIS3521: 5'-GTT-CTC-GCT-GGT-GAG-TTT-CA-3', with modifications as noted below.

The primer support was slurried and packed in toluene.
The cycle for addition of each nucleotide was:
Detritylation: DCA in toluene;
Column wash: toluene (3 column volumes, 81 ml) followed by acetontrile (1 column volume, 27 ml);
Coupling: phosphoramidite in acetonitrile;
Acetonitrile push/wash;
Oxidation: phenyl acetyl disulfide in acetonitrile;
Toluene push (instead of usual acetonitrile push);
Capping: Reagent A;
Capping: Reagent B;
Toluene wash (1.5 CV, ~40.4 ml).

This cycle is repeated for each of the nucleotides to be coupled to the oligonucleotide. Synthesis completes with the final toluene wash, after which the protocol for cleaving the oligonucleotide from the support was conducted as outlined in Example 1, above.

Table 2 contains the peak data for the HPLC of ISIS3521 by the procedure of Example 2.

TABLE 2

| # | Retention Time (min.) | Area (uV* sec) | Height (uV) | % of Total Area |
|---|---|---|---|---|
| 1 | 15.517 | 0.00671 | 0.00004 | 0.042 |
| 2 | 15.688 | 0.01959 | 0.00009 | 0.122 |
| 3 | 16.004 | 0.03287 | 0.00025 | 0.206 |
| 4 | 16.219 | 0.02150 | 0.00015 | 0.134 |
| 5 | 16.535 | 0.01368 | 0.00006 | 0.086 |
| 6 | 17.074 | 0.01152 | 0.00013 | 0.118 |
| 7 | 17.074 | 0.01152 | 0.00008 | 0.072 |
| 8 | 17.279 | 0.04077 | 0.00020 | 0.255 |
| 9 | 17.685 | 0.02992 | 0.00012 | 0.187 |
| 10 | 18.231 | 0.31423 | 0.00203 | 1.963 |
| 11 | 18.459 | 0.36053 | 0.00266 | 2.253 |
| 12 | 18.693 | 0.26639 | 0.00191 | 1.664 |
| 13 | 18.925 | 0.41764 | 0.00339 | 2.610 |
| 14 | 19.107 | 0.48205 | 0.00414 | 3.011 |
| 15 | 19.485 | 0.64188 | 0.00420 | 4.011 |
| 16 | 19.688 | 0.25966 | 0.00204 | 1.622 |
| 17 | 20.053 | 0.43284 | 0.00303 | 2.705 |
| 18 | 20.270 | 0.29293 | 0.00167 | 1.830 |
| 19 | 20.647 | 0.29594 | 0.00175 | 1.849 |
| 20 | 20.982 | 0.72754 | 0.00452 | 4.546 |
| 21 | 21.319 | 0.44425 | 0.00327 | 2.775 |
| 22 | 21.663 | 0.50899 | 0.00300 | 3.181 |
| 23 | 22.098 | 10.30827 | 0.03784 | 64.407 |
| 24 | 24.259 | 0.01264 | 0.00004 | 0.079 |
| 25 | 24.983 | 0.04359 | 0.00013 | 0.272 |
| Total | — | 16.00492 | 0.07676 | 100.00 |

Overall, approximately 100,000 ODs of crude ISIS3521 were obtained, which was approximately 67% full-length. In a second iteration, approximately 100,000 ODs of approximately 58% full-length, crude ISIS3521 were obtained using the procedure outlined above.

Example 3

0.75 mmole Synthesis of ISIS-3521

A procedure similar to that employed in Example 2, above, was followed for preparation of 0.75 mmole of ISIS-3521: 5'-GTT-CTC-GCT-GGT-GAG-TTT-CA-3', with modifications as noted below.

The primer support was slurried and packed in toluene.
The cycle for addition of each nucleotide was:
Detritylation: DCA in toluene;
Column wash: toluene (3 column volumes, 81 ml) followed by acetonitrile (1 column volume, 27 ml);
Coupling: phosphoramidite in acetonitrile;
Acetonitrile push/wash;
Oxidation: phenyl acetyl disulfide in acetonitrile;
Capping: Reagent A; (acetonitrile/toluene push eliminated) Capping: Reagent B;
Toluene wash (1.5 CV, ~40.4 ml).

This cycle was repeated for each of the nucleotides to be coupled to the oligonucleotide. Synthesis was completed with the final toluene wash, after which the protocol for cleaving the oligonucleotide from the support was conducted as outlined in Example 1, above.

Overall, approximately 100,000 ODs of crude, 65% full-length, ISIS-3521 were obtained.

The person having skill in the art will recognize that the foregoing experiments demonstrate the surprising suitability of replacing the art-recognized acetonitrile column/wash or reagent push with a toluene column wash and/or reagent push. In some embodiments, it was possible to eliminate a reagent push altogether, thereby obtaining additional solvent savings.

The person having skill in the art will recognize that further embodiments are possible within the general scope of the foregoing description and the attached drawings and claims, and it would be within the skill of such skilled person to practice the invention as generally described herein.

Example 4

Synthesis of Larger Scale Batches

Larger scale batches of oligonucleotide, e.g. ISIS-2302 or ISIS-3521 may be synthesized by scaling the reagents, solvents, primer support, in proportion to the increased quantity of desired product. For example, an 800 mmole batch may be prepared in the following manner:

The quantity of primer support having a loading value of 90 μmol/g necessary to obtain 80 mmol of the 3'-terminal nucleoside attached to solid support may be calculated to be 8889 g of support. Approximately 9000 g of support, may be weighed into an appropriate container and 4-5 L of acetonitrile per 100 g of support may be added to produce a slurry. The support may then be packed into a suitable column, which may then be attached to an Amersham Akta synthesizer per established procedures. A new synthesis result directory may then be created to produce the desired sequence.

Deblock solution, activator solution, deoxyphosphoramidite solutions, thiation solution, capping solution A, capping solution B, triethylamine solution, acetonitrile and toluene may then be loaded into appropriate reservoirs. The synthesis cycle may be conducted as follows:
Detritylation: DCA in toluene;
Column wash: toluene;
Coupling: phosphoramidite in acetonitrile;
Acetonitrile push/wash;
Oxidation: phenyl acetyl disulfide in acetonitrile;
Acetonitrile push;
Capping: Reagent A;
Capping: Reagent B;
Toluene wash;

This cycle should be repeated for each of the phosphoramidites to be coupled to the oligonucleotide. Synthesis will be complete with the final toluene wash.

Following completion of synthesis, the column may be unpacked according to an established procedure and the contents of the column may be transferred to a 100 L container. Ammonium hydroxide solution, approximately 50 L, may be added to the support and stirred to form a slurry. The slurry may then be evenly divided among ten graduated, 20 L carboys, and then diluted with about 8-9 L of additional ammonium hydroxide, refrigerated for three days (~5-10° C.) and then incubated at 50-60° C. for 23.5 h, after which they may again be refrigerated. The cooled solutions may then be decanted through a large Buchner funnel containing a filter into appropriate-sized clean glass carboys. Approximately 10 L of 50% water/purified ethanol (v/v) may then be added to each carboy support-containing support. Each carboy may then be shaken to slurry, and then filtered as above.

The filtrate may be processed to produce about $107 \times 10^6$ O.D.s (260 nm) of free, purified, 5'-blocked oligonucleotide, which may be further processed to produce free, purified, deblocked oligonucleotide.

The artisan will understand that, by modifying the foregoing procedures, e.g. by changing the sequence, the substitution pattern of the oligonucleotide, the starting primer support, etc., the foregoing methodology may be employed to make batches of oligonucleotide having a variety of characteristics in quantities on the order of from about 0.8 mmole to on the order of about 1 mole.

Example 5

80 mmole Synthesis: Other Alternative Solvents

Another 80 mmole synthesis of ISIS-2302 or ISIS-3521 may be conducted as in Example 1, above, except that the solvent wash will be selected from pyridine, xylenes, hexanes, heptanes or mixtures thereof instead of toluene. The results are expected to be similar to those of Example 1.

Example 6,

80 mmole Synthesis of Gapmers

An 80 mmole synthesis of a gapmer may be conducted per Example 1 above, except that the primer support is 2'-methoxyethyl-2'-deoxyadenosine-linked support, the first four and the last five phosphoramidites will be replaced with their analogous 2'-methoxyethyl-2'-deoxyribonucleosyl amidites. The resulting compound is expected to have the following sequence:

5'-GCC-CAA-GCT-GGC-ATC-CGT-CA-3', wherein each of the underlines indicates a 2'-O-methoxyethyl-2'-deoxyribonucleosyl residue.

All references cited herein are expressly incorporated herein by reference.

What is claimed is:

1. A method of manufacturing an oligonucleotide comprising a pentavalent phosphate triester, said method comprising:

(a) providing a 5' blocked-nucleoside;
   (b) deblocking the 5' blocked-nucleoside to form a 5' OH-nucleoside;
   (c) coupling the 5' OH-nucleoside with a phosphoramidite of formula (IV)

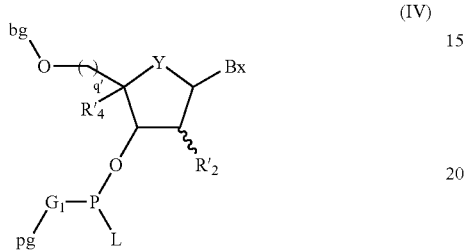

(IV)

wherein Y is O, S, $CH_2$, CHF, $CF_2$ or —CH═CH—;
   bg is a 5'-blocking group;
   $R'_2$ is H, OZ, a 2'-substituent, or together with $R'_4$ forms a bridge; $R'_4$ is H, OZ, a 2'-substituent, or together with $R'_2$ forma a bridge; Z is H or a removable protecting group;
   Bx is a nucleobase;
   pg is a phosphorus protecting group; each G is 0 or S;
   L is an amine leaving group;
   $G_1$ is 0 or S; and
   q' is 0 or 1;

to form an oligonucleotide comprising a trivalent phosphite triester; and (d) oxidizing the oligonucleotide comprising a trivalent phosphite triester to form the oligonucleotide comprising a pentavalent phosphate triester;

wherein at least a wash between any of the steps above is with a solvent wash comprising a toluene, pyridine, lutidine, hexane, cyclohexane, cyclohexene, a halogenated benzene, alkylated benzenes, a haloalkylbenzene, acetone, ethylacetate, methanol, ethanol, phenol, cyclic ethers, acyclic ethers, halogenated alkanes or mixtures thereof.

2. The method of claim 1, wherein a wash between any of the steps above is with at least one solvent wash comprising a toluene.

3. The method of claim 1, wherein the 5' blocked-nucleoside is linked to another nucleoside.

4. The method of claim 1, wherein the 5' blocked-nucleoside is linked to a solid support.

5. The method of claim 1 wherein the 5' blocked-nucleoside comprises a sugar moiety and a base.

6. The method of claim 1, wherein the solvent wash comprises a toluene and an acetonitrile.

7. The method of claim 1, wherein the solvent wash is substantially free of an acetonitrile.

8. A method of manufacturing a compound of Formula I:

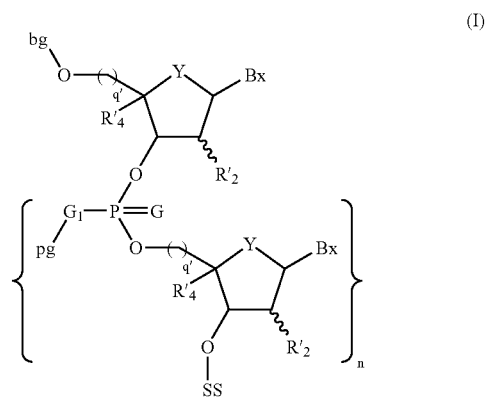

(I)

wherein Y is O, S, $CH_2$, CHF, $CF_2$ or —CH═CH—;
bg is a 5'-blocking group;
n is a positive integer;
each $R'_2$ is, independently, H, OZ, a 2'-substituent, or together with $R'_4$ forms a bridge; each $R'_4$ is, independently, H, OZ, a 2'-substituent, or together with $R'_4$ forms a bridge; each $R'_4$ is, protecting group;
each Bx is independently a nucleobase;
each pg is independently a phosphorus protecting group;
each G is 0 or S;
each $G_1$ is 0 or S;
each q' is independently 0 or 1; and
SS is a solid support; said process comprising:
   (a) contacting a compound of Formula II:

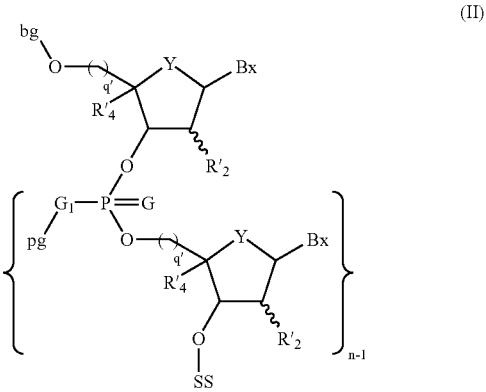

(II)

with a deblocking agent to produce a compound of Formula III:

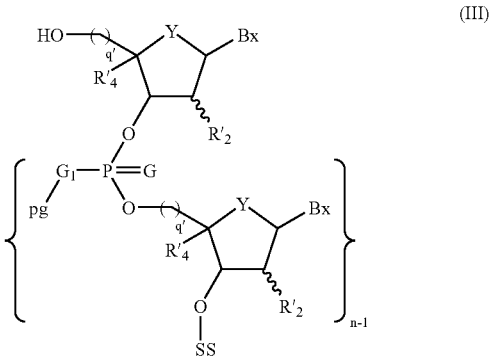

(III)

(b) contacting the compound of Formula III with a first solvent wash;

(c) contacting the compound of Formula III with a compound of Formula IV:

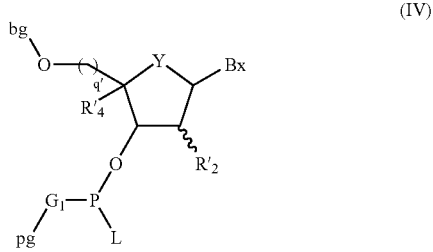

(IV)

wherein L is a leaving group, to form a compound of Formula V:

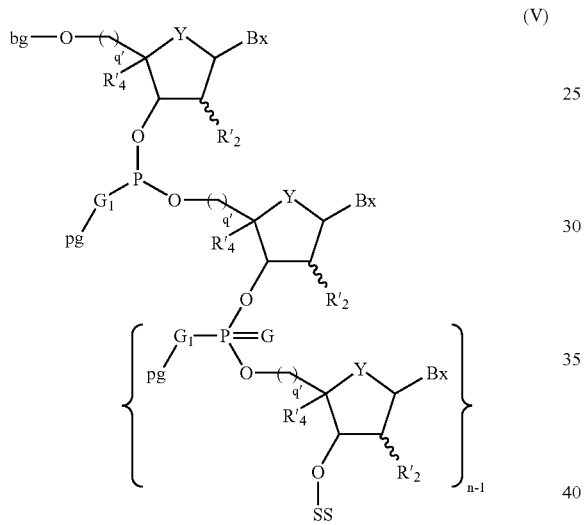

(V)

(d) contacting the compound of Formula V with a second solvent wash; and (e) contacting the compound of Formula V with an oxidation reagent to form the compound of Formula I;

wherein at least one of the first and second solvent wash comprises a toluene, pyridine, lutidine, hexane, cyclohexane, cyclohexene, a halogenated benzene, alkylated benzenes, a haloalkylbenzene, acetone, ethylacetate, methanol, ethanol, phenol, cyclic ethers, acyclic ethers, halogenated alkanes or mixtures thereof.

9. The method of claim 8, wherein the first solvent wash comprises the toluene.

10. The method of claim 8, wherein the first solvent wash comprises the toluene and an acetonitrile.

11. The method of claim 8, wherein the first solvent wash is substantially free of an acetonitrile.

12. The process according to claim 8, wherein the second solvent wash comprises a toluene.

13. The method of claim 8, wherein the second solvent wash comprises the toluene and an acetonitrile.

14. The method of claim 8, wherein the second solvent wash is substantially free of an acetonitrile.

15. The method of claim 8, after (e), further comprising:
(f) contacting the compound of Formula I with a third solvent wash.

16. The method of claim 15, after (f), further comprising:
(g) capping any compound of Formula III that has not reacted with the compound of Formula IV.

17. The method of claim 15, wherein the third solvent wash comprises at least one of a toluene, an acetonitrile, or mixture thereof.

18. The method of claim 15, wherein the third solvent wash is substantially free of an acetonitrile.

19. The method of claim 8, after (e), further comprising capping any compound of Formula IV that has not reacted with the compound of Formula IV.

20. The process according to claim 8, wherein each Y is O.

21. The process of claim 8, wherein n is about 7 to about 79.

22. The process of claim 8, wherein each $R'_2$ is H or a 2'-substituent.

23. The process of claim 8, wherein each $R'_2$ is H or a 2'-substituent, said 2'-substituent being a member of the group consisting of 2'-O—$CH_3$, 2'-O—$CH_2CH_2OCH_3$, or 2'-O—$(CH_2)_3NH_2$.

24. The process of claim 8, wherein said 2'-substituent is 2'-$OCH_2CH_2OCH_3$.

25. The process of claim 8, wherein each q' is 1.

26. The process of claim 8, wherein each G is S.

27. A process of claim 8, further comprising cleaving the compound of Formula I from the solid support to form a compound of Formula X:

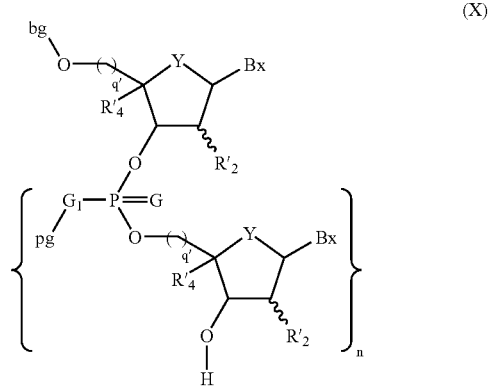

(X)

wherein the variables have the same definitions as in claim 8.

* * * * *

UNITED STATES PATENT AND TRADEMARK OFFICE
CERTIFICATE OF CORRECTION

PATENT NO. : 7,276,599 B2 Page 1 of 1
APPLICATION NO. : 10/858917
DATED : October 2, 2007
INVENTOR(S) : Max N. Moore et al.

It is certified that error appears in the above-identified patent and that said Letters Patent is hereby corrected as shown below:

Title Page:
Item [74], Attorney, Agent, or Firm, please insert --; Isis Patent Department--;

Column 69, Claim 1, line 25, please delete "0" and insert therefor --O--;

Column 69, Claim 1, line 30, please delete "forma" and insert therefor --forms--;

Column 69, Claim 1, line 35, please delete "0" and insert therefor --O--;

Column 69, Claim 1, line 37, please delete "0" and insert therefor --O--;

Column 70, Claim 8, line 25, please delete "R'$_4$" and insert therefor --R'$_2$--;

Column 70, Claim 8, line 26, please delete "each R'$_4$ is," and insert therefor --Z is H or a removable--;

Column 70, Claim 8, line 29, please delete "0" and insert therefor --O--;

Column 70, Claim 8, line 30, please delete "G, is 0" and insert therefor --G$_1$ is O--;

Column 72, Claim 20, line 21, please delete "0" and insert therefor --O--.

Signed and Sealed this

Twenty-ninth Day of July, 2008

JON W. DUDAS
*Director of the United States Patent and Trademark Office*

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
gcccaagctg gcatccgtca                                       20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
gttctcgctg gtgagtttca                                       20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
gttctcgctg gtgagtttca                                       20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: (1)..(5)
<223> OTHER INFORMATION: 2'-O-methoxyethyl-2'-deoxyribonucleosyl residue
<220> FEATURE:
<221> NAME/KEY: modified_base
<222> LOCATION: (16)..(20)
<223> OTHER INFORMATION: 2'-O-methoxyethyl-2'-deoxyribonucleosyl residue

<400> SEQUENCE: 4
gcccaagctg gcatccgtca                                       20